(12) United States Patent
Kim

(10) Patent No.: US 11,745,012 B2
(45) Date of Patent: Sep. 5, 2023

(54) METHOD AND PROGRAM FOR NAVIGATING TMS STIMULATION

(71) Applicant: NEUROPHET INC., Seoul (KR)

(72) Inventor: Dong Hyeon Kim, Seoul (KR)

(73) Assignee: NEUROPHET INC., Seoul (KR)

( * ) Notice: Subject to any disclaimer, the term of this patent is extended or adjusted under 35 U.S.C. 154(b) by 770 days.

(21) Appl. No.: 16/814,835

(22) Filed: Mar. 10, 2020

(65) Prior Publication Data

US 2020/0214569 A1   Jul. 9, 2020

Related U.S. Application Data

(63) Continuation of application No. PCT/KR2018/010169, filed on Aug. 31, 2018.

(30) Foreign Application Priority Data

Sep. 11, 2017   (KR) .................. 10-2017-0115778

(51) Int. Cl.

| A61N 1/36 | (2006.01) |
| G16H 20/30 | (2018.01) |
| G16H 50/20 | (2018.01) |
| A61B 5/00 | (2006.01) |
| A61N 2/00 | (2006.01) |
| A61N 2/02 | (2006.01) |
| A61B 5/055 | (2006.01) |
| A61B 34/10 | (2016.01) |
| G16H 50/50 | (2018.01) |

(52) U.S. Cl.
CPC ........ *A61N 1/36025* (2013.01); *A61B 5/0036* (2018.08); *A61B 5/055* (2013.01);
(Continued)

(58) Field of Classification Search
CPC . A61B 2576/026; A61B 34/10; A61B 5/0035; A61B 5/0036; A61B 5/0042;
(Continued)

(56) References Cited

U.S. PATENT DOCUMENTS

| 6,827,681 B2* | 12/2004 | Tanner ................... A61B 5/055 600/9 |
| 6,830,544 B2* | 12/2004 | Tanner ................... A61B 5/055 607/45 |

(Continued)

FOREIGN PATENT DOCUMENTS

| JP | WO2015-122369 A1 | 3/2017 |
| JP | 6161004 B2 | 7/2017 |

(Continued)

OTHER PUBLICATIONS

Opitz, A.& Legon, W. (2013). Physiological observations validate finite element models for estimating subject-specific electric field distributions induced by transcranial magnetic stimulation of the human motor cortex. NeuroImage, 81, 253-264 http://doi.org/10.1016/j.neuroimage.2013.04.067 (Year: 2013).*

(Continued)

*Primary Examiner* — Thaddeus B Cox
*Assistant Examiner* — Marc D. Honrath
(74) *Attorney, Agent, or Firm* — Studebaker & Brackett PC

(57) ABSTRACT

Disclosed is a transcranial magnetic stimulation (TMS) stimulation navigation method comprising the steps of: acquiring a stimulation target point in the brain of a subject to which an electrical stimulus is to be applied; acquiring data on the spatial distribution of a magnetic vector potential of a coil for a TMS procedure; acquiring, from the spatial distribution, at least one parameter for acquiring an optimal stimulation condition for the stimulation target point; and by using the acquired parameter, calculating a position and direction of the coil satisfying the optimal stimulation condition for the stimulation target point.

14 Claims, 21 Drawing Sheets
(14 of 21 Drawing Sheet(s) Filed in Color)

(52) U.S. Cl.
CPC ............ *A61B 5/7267* (2013.01); *A61B 34/10* (2016.02); *A61N 1/36031* (2017.08); *A61N 2/006* (2013.01); *A61N 2/02* (2013.01); *G16H 20/30* (2018.01); *G16H 50/20* (2018.01); *G16H 50/50* (2018.01); *A61B 2576/026* (2013.01)

(58) Field of Classification Search
CPC ....... A61B 5/0064; A61B 5/055; A61B 5/369; A61B 5/6898; A61B 5/7267; A61B 5/7425; A61N 1/08; A61N 1/36025; A61N 1/36031; A61N 1/40; A61N 2/006; A61N 2/02; G16H 20/30; G16H 30/40; G16H 50/20; G16H 50/50
See application file for complete search history.

(56) References Cited

U.S. PATENT DOCUMENTS

| | | | |
|---|---|---|---|
| 7,008,370 B2 * | 3/2006 | Tanner | A61B 5/055 600/9 |
| 7,239,910 B2 * | 7/2007 | Tanner | A61N 2/02 607/45 |
| 7,471,974 B2 * | 12/2008 | Tanner | A61N 2/02 600/407 |
| 7,711,431 B2 * | 5/2010 | Tanner | A61N 2/02 607/45 |
| 10,292,645 B2 * | 5/2019 | Saitoh | A61B 5/4064 |

FOREIGN PATENT DOCUMENTS

| | | |
|---|---|---|
| KR | 10-2008-0065577 A | 7/2008 |
| KR | 10-2015-0002770 A | 1/2015 |
| KR | 10-2015-0135447 A | 12/2015 |
| KR | 10-2016-0122733 A | 10/2016 |

OTHER PUBLICATIONS

An Office Action; "Notice of Reasons for Refusal," mailed by the Japanese Patent Office dated Apr. 6, 2021, which corresponds to Japanese Patent Application No. 2020-514534 and is related to U.S. Appl. No. 16/814,835 with with English translation.

International Search Report issued in PCT/KR2018/010169; dated Nov. 27, 2018.

* cited by examiner

FIG. 6
600 610
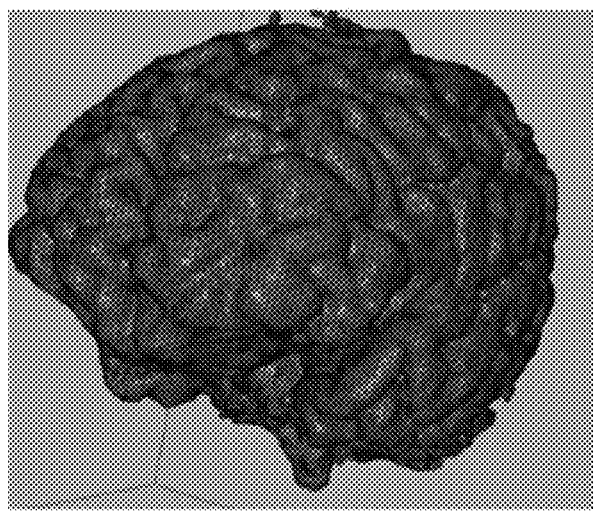
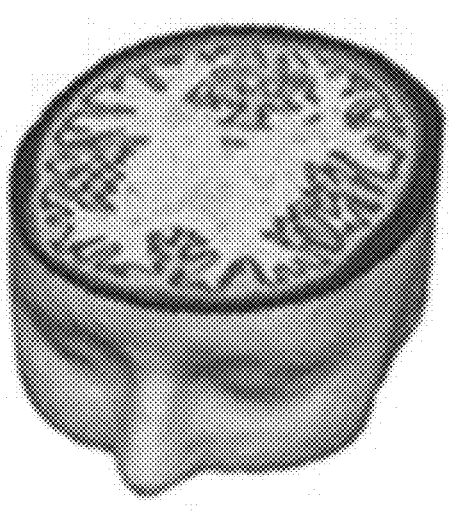

METHOD AND PROGRAM FOR NAVIGATING TMS STIMULATION

CROSS-REFERENCE TO RELATED APPLICATIONS

The present application is a continuation of International Patent Application No. PCT/KR2018/010169, filed Aug. 31, 2018 which is based upon and claims the benefit of priority to Korean Patent Application No. 10-2017-0115778 filed on Sep. 11, 2017. The disclosures of the above-listed applications are hereby incorporated by reference herein in their entirety.

BACKGROUND

Embodiments of the inventive concept described herein relate to a transcranial magnetic stimulation (TMS) stimulation navigation method and a program.

A magnetic resonance imaging (MRI) system is a device which expresses an intensity of a magnetic resonance (MR) signal for a radio frequency (RF) signal generated by a magnetic field of a specific intensity in contrast to acquire an image for a tomographic portion of an object. For example, when an RF signal which resonates only specific atomic nuclei (e.g., hydrogen atomic nuclei or the like) is instantaneously irradiated to the object after the object is laid in a strong magnetic field and is then stopped, an MR signal is emitted from the specific atomic nuclei, and the MRI system may receive the MR signal and may acquire an MR image. The MR signal refers to an RF signal radiated from the object. A level of the MR signal may be determined by a concentration of certain atoms (e.g., hydrogen or the like) included in the object, a relaxation time T1, a relaxation time T2, and the flow of blood flows or the like.

The MRI system includes features different from other imaging devices. Unlike the imaging devices, such as a computerized tomography (CT) device, in which acquisition of an image depends on a direction of detection hardware, the MRI system may acquire a 2D image or a 3D volume image oriented toward any point. Furthermore, unlike a CT device, an X-ray device, a positron emission tomography (PET) device, and a single photon emission computed tomography (SPECT) device, the MRI system does not expose a radioactive ray to an object and an inspector, and may acquire an image having a high soft tissue contrast to acquire a neurological image, an intravascular image, a musculoskeletal image, an oncologic image, and the like, in which it is important to clearly describe abnormal tissues.

Transcranial magnetic stimulation (TMS) is a non-invasive treatment method for the nervous system, which may treat nervous disease without mediation or invasive treatment. The TMS may apply electrical stimulation to the object using a change in magnetic field.

In general, the TMS was treated in such a manner as to apply electrical stimulation to a stimulation point known on a clinical basis or on a theoretical basis or determine a stimulation position while a user gradually moves the stimulation position. Thus, it is difficult to reflect a type of a coil used for procedure or a difference in body structure between persons, and it is difficult to directly identify the effect according to procedure.

Furthermore, a brain disease treatment method through an electroencephalogram (EEG), capable of measuring an electrical activity according to the activity of the brain of the object, and electrical stimulation is widely used. However, there is a need for development of a guide method for reflecting a shape of the head, which differs for each person, in the EEG and the electrical stimulation like the TMS.

SUMMARY

Embodiments of the inventive concept provide a TMS stimulation navigation method and a program.

The technical objects of the inventive concept are not limited to the above-mentioned ones, and the other unmentioned technical objects will become apparent to those skilled in the art from the following description.

According to an exemplary embodiment, a TMS stimulation navigation method may include acquiring a stimulation target point to apply electrical stimulation on the brain of an object, acquiring information about a spatial distribution of a magnetic vector potential of a coil for TMS procedure, acquiring one or more parameters for acquiring an optimal stimulation condition for the stimulation target point, from the spatial distribution, and calculating a position and direction of the coil, the position and direction satisfying the optimal stimulation condition for the stimulation target point, using the acquired one or more parameters.

Furthermore, the acquiring of the information about the spatial distribution may include acquiring information by visualizing a magnetic vector potential using a magnetic dipole according to a shape of the coil for TMS procedure.

Furthermore, the optimal stimulation condition for the stimulation target point may be a condition where an intensity of a magnetic field applied to the stimulation target point by the coil for TMS procedure becomes maximum.

Furthermore, the acquiring of the one or more parameters may include acquiring an optimal point having the highest magnetic vector potential in the spatial distribution and acquiring an optimal vector which is a normal vector where multiplication with a gradient at the optimal point becomes minimum among normal vectors where the optimal point is a start point.

Furthermore, the calculating of the position and direction of the coil may include calculating the position and direction of the coil such that the stimulation target point is closest in the direction of the optimal vector from the optimal point.

Furthermore, the TMS stimulation navigation method may further include simulating a state where electrical stimulation induced from a magnetic field of the coil for TMS procedure is propagated in the brain of the object, when the coil for TMS procedure is located at the calculated position in the calculated direction.

Furthermore, the simulating may include acquiring a brain magnetic resonance imaging (MRI) image of the object, generating a three-dimensional brain map of the object, the three-dimensional brain map being capable of simulating a process of delivering electrical stimulation to the brain of the object, based on properties of each of a plurality of regions included in the brain MRI image, and simulating a state where the electrical stimulation is propagated in the brain of the object, using the generated three-dimensional brain map.

Furthermore, the generating of the three-dimensional brain map may include generating a three-dimensional stereoscopic image composed of a plurality of meshes, the three-dimensional stereoscopic image being capable of simulating a process of delivering electrical stimulation to the brain of the object.

Furthermore, the simulating may include visualizing a state where electrical stimulation induced from a magnetic field of the coil for TMS procedure is propagated in the brain of the object, using the three-dimensional stereoscopic image.

According to an exemplary embodiment, a computer program may be combined with a computer which is hardware and may be stored in a computer-readable storage medium to perform the TMS stimulation navigation method according to the disclosed embodiment.

The other detailed items of the inventive concept are described and illustrated in the specification and the drawings.

BRIEF DESCRIPTION OF THE FIGURES

The patent or application file contains at least one drawing executed in color. Copies of this patent or patent application publication with color drawing(s) will be provided by the Office upon request and payment of the necessary fee.

The above and other objects and features will become apparent from the following description with reference to the following figures, wherein like reference numerals refer to like parts throughout the various figures unless otherwise specified, and wherein:

FIG. 6 is a drawing illustrating an example of a three-dimensional brain image generated from a brain MRI image of an object;

DETAILED DESCRIPTION

Figure 1:
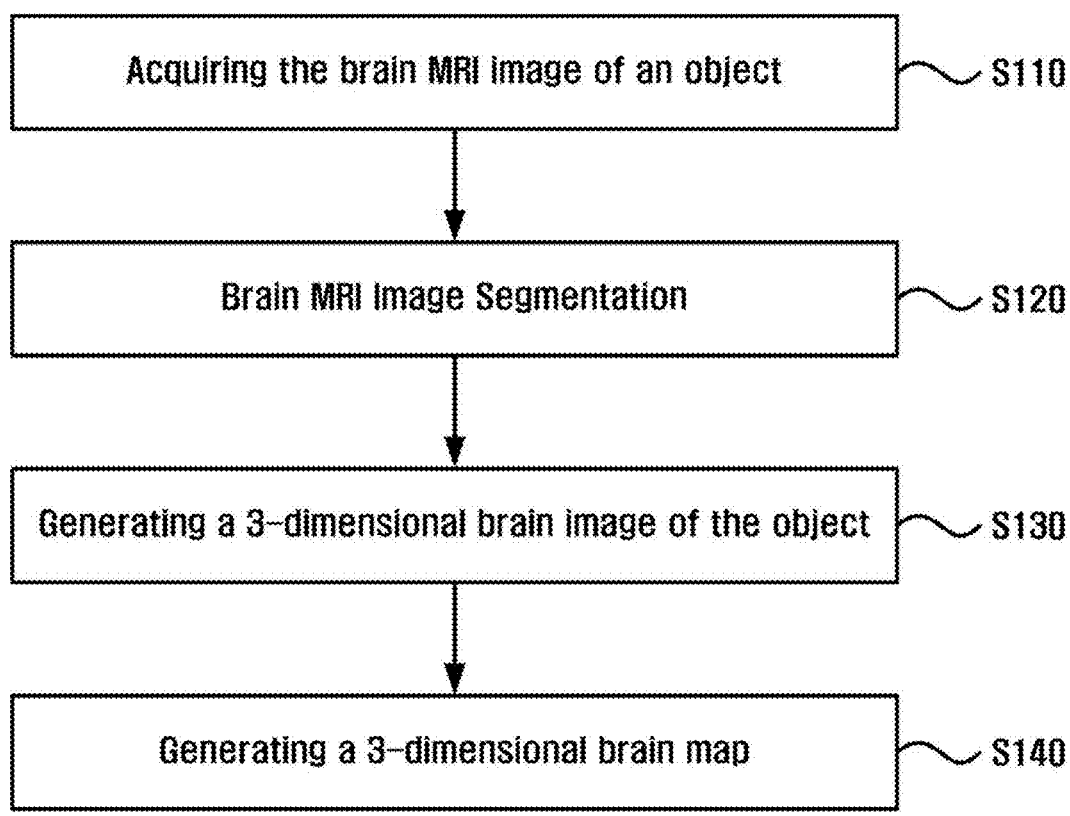
FIG. 1 is a flowchart illustrating a method for generating a three-dimensional brain map according to an embodiment.

Advantages, features, and methods of accomplishing the same will become apparent with reference to embodiments described in detail below together with the accompanying drawings. However, the inventive concept is not limited by embodiments disclosed hereinafter, and may be implemented in various forms. Rather, these embodiments are provided to so that this disclosure will be through and complete and will fully convey the concept of the invention to those skilled in the art, and the inventive concept will only be defined by the appended claims.

Terms used in the specification are used to describe embodiments of the inventive concept and are not intended to limit the scope of the inventive concept. In the specification, the terms of a singular form may include plural forms unless otherwise specified. The expressions "comprise" and/or "comprising" used herein indicate existence of one or more other elements other than stated elements but do not exclude presence of additional elements. Like reference numerals designate like elements throughout the specification, and the term "and/or" may include each of stated elements and one or more combinations of the stated elements. The terms such as "first" and "second" are used to describe various elements, but it is obvious that such elements are not restricted to the above terms. The above terms are used only to distinguish one element from the other. Thus, it is obvious that a first element described hereinafter may be a second element within the technical scope of the inventive concept.

Unless otherwise defined herein, all terms (including technical and scientific terms) used in the specification may have the same meaning that is generally understood by a person skilled in the art. Also, terms which are defined in a dictionary and commonly used should be interpreted as not in an idealized or overly formal detect unless expressly so defined.

The term "unit" or "module", as used herein, means, but is not limited to, a software or hardware component, such as field-programmable gate array (FPGA) or application-specific integrated circuit (ASIC), which performs certain tasks. However, the "unit" or "module" is not limited to software or hardware. A "unit" or "module" may advantageously be configured to reside on the addressable storage medium and configured to execute on one or more processors. Thus, a "unit" or "module" may include, by way of example, components, such as software components, object-oriented software components, class components and task components, processes, functions, attributes, procedures, subroutines, segments of program codes, drivers, firmware, microcode, circuitry, data, databases, data structures, tables, arrays, and variables. The functionality provided for in the components and "unit" or "module" may be combined into fewer components and "unit" or "module" or further separated into additional components and "unit" or "module".

In the present specification, the "object" may include a human, an animal, or a part of a human or animal. For example, the object may be an organ, such as the liver, the heart, the womb, the brain, a breast, or the abdomen, or a blood vessel. Furthermore, the "object" may include a phantom. The phantom may refer to a material having a volume which is approximately the same as a density and an effective atomic number of an organism, which may include a spherical phantom having properties similar to the human body.

Furthermore, in the present specification, the "user" may be a medical doctor, a nurse, a medical laboratory technologist, a medical imaging expert, or the like, as a medical expert, or may be a technician who repairs a medical apparatus, but not limited thereto.

Furthermore, in the present specification, the "magnetic resonance (MR) image" may refer to an image of an object acquired using the nuclear magnetic resonance principle.

Hereinafter, an embodiment of the inventive concept will be described in detail with reference to the accompanying drawings.

Figure 3:
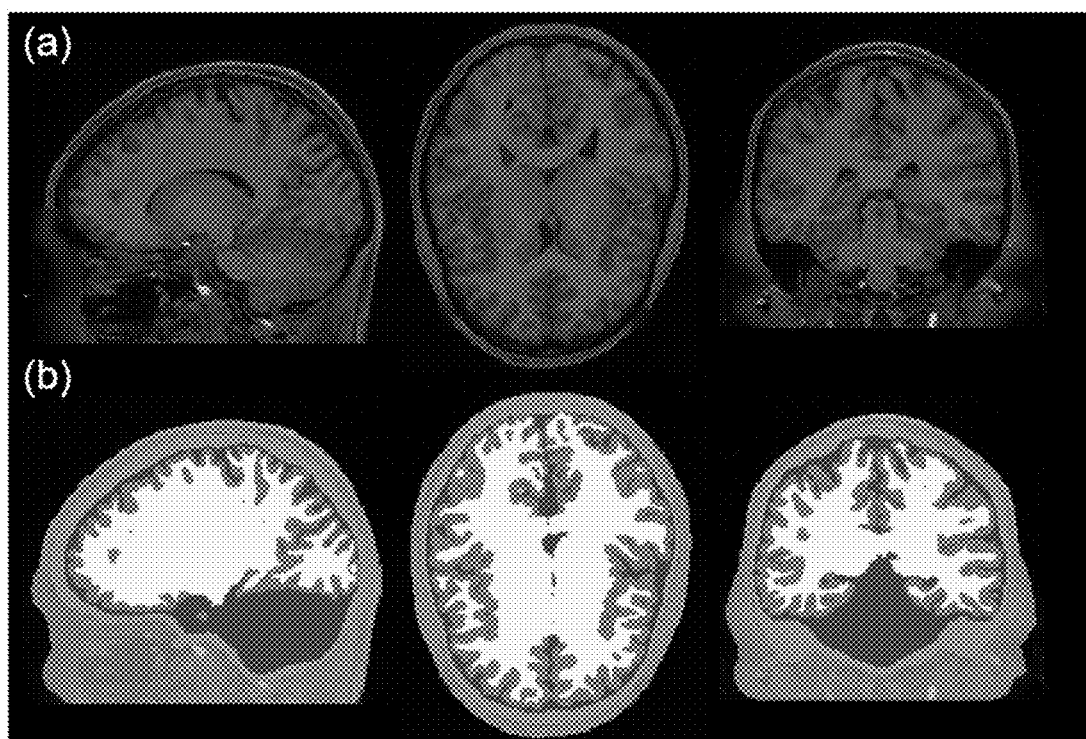
FIG. 3 is a drawing illustrating the result of performing segmentation of a brain MRI image.
Figure 4:
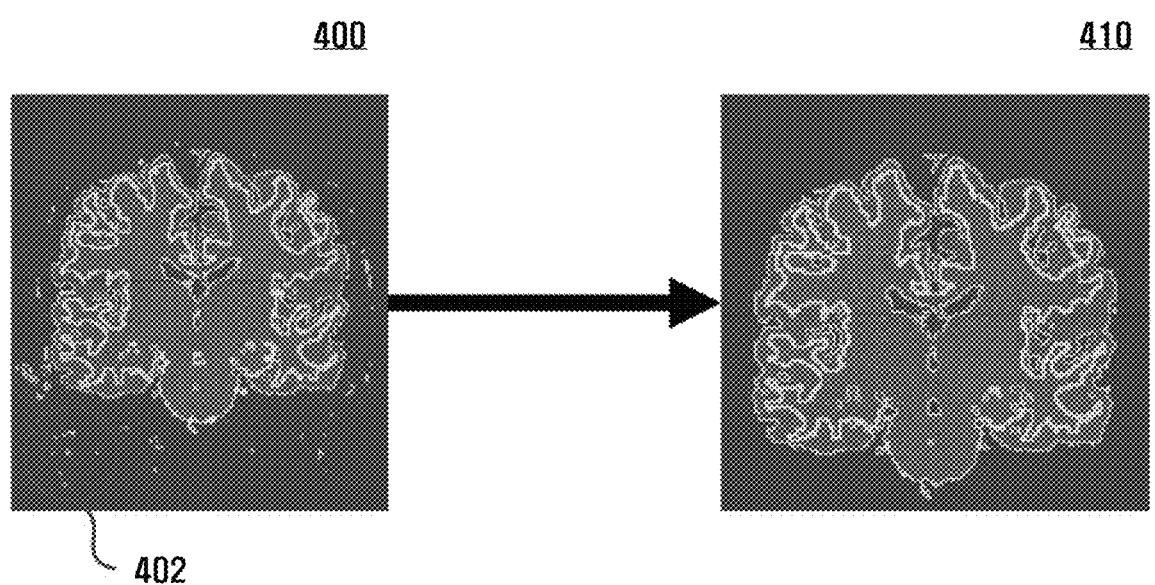
FIG. 4 is a drawing illustrating an example of a connected component-based noise rejection method.
Figure 5:
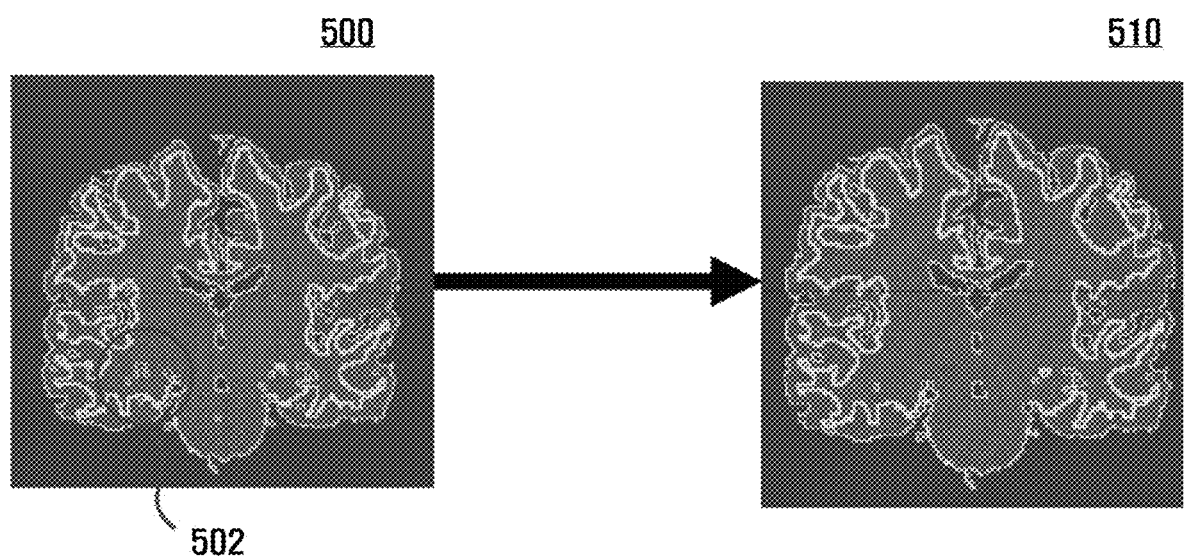
FIG. 5 is a drawing illustrating an example of a post-processing scheme using hole rejection.

FIG. 1 is a flowchart illustrating a method for generating a three-dimensional brain map according to an embodiment. FIG. 3 is a drawing illustrating the result of performing segmentation of a brain MRI image. FIG. 4 is a drawing illustrating an example of a connected component-based noise rejection method. FIG. 5 is a drawing illustrating an example of a post-processing scheme using hole rejection. FIG. 6 is a drawing illustrating an example of a three-dimensional brain image generated from a brain MRI image of an object.

The method shown in FIG. 1 shows operations, performed by a computer, in time series. The computer in the present specification may be used as the meaning including a computing device including at least one processor.

In operation S110, the computer may acquire a brain magnetic resource imaging (MRI) image of an object.

In an embodiment, the computer may be a workstation connected with an MRI image acquisition device, which may directly acquire a brain MRI image of the object from the MRI image acquisition device.

Furthermore, the computer may acquire a brain MRI image of the object from an external server or another computer.

In the disclosed embodiment, the brain MRI image of the object may refer to an MRI image acquired by capturing a head part including the brain of the object. In other words, the brain MRI image of the object may refer to an MRI image including the skull and scalp of the object as well as the brain of the object.

In operation S120, the computer may segment (partition) the brain MRI image acquired in operation S110 into a plurality of regions.

In an embodiment, the computer may segment the brain MRI image acquired in operation S110 for each part. For example, the computer may segment the brain MRI image acquired in operation S110 into the white matter, the gray matter, the cerebrospinal fluid, the skull, and the scalp, but the types capable of segmenting the brain MRI image are not limited thereto.

In an embodiment, the computer may input the brain MRI image of the object to a model learned using a plurality of processed brain MRI images to acquire a segmented brain MRI image of the object.

In an embodiment, the processed brain MRI image may be an image acquired by labeling each of the plurality of regions included in the brain MRI image. Furthermore, the learned model may be a model for receiving the brain MRI image and outputting a segmented brain MRI image.

In an embodiment, the learned model may refer to a model learned using machine learning and may refer to a model particularly learned using deep learning.

In an embodiment, the learned model may be, but is not limited to, a model including one or more batch normalization layers, an activation layer, and a convolution layer.

In an embodiment, the learned model may be configured to include a horizontal pipeline configured with a plurality of blocks which extract a high-level characteristic from a low-level characteristic of an MRI image and a vertical pipeline which collects and segments characteristics extracted by the horizontal pipeline and perform segmentation of MRI with relatively degraded image quality.

Referring to FIG. 3, the result 300(b) of segmenting a brain MRI image 300a is shown.

In an embodiment, the computer may post-process the segmented result.

In an embodiment, the computer may perform connected component-based noise rejection. The connected component-based noise rejection method may be used to improve the result of segmentation performed using a convolution neural network (CNN).

Referring to FIG. 4, an example of the connected component-based noise rejection method is shown.

The computer may remove the other components 402, except for a connected component which is the largest chunk, from a segmentation image 400 to acquire an improved segmentation image 410.

In an embodiment, the computer may perform hole rejection. The hole rejection may be used to remove a hole which is one of errors of convolution neural network based segmentation.

Referring to FIG. 5, an example of a post-processing scheme using the hole rejection is shown.

The computer may remove at least a portion of a hole 502 included in a segmentation image 500 to acquire an improved segmentation image 510.

In operation S130, the computer may generate a three-dimensional brain image of the object, including the plurality of segmented regions, using the brain MRI image of the object segmented in operation S120.

Referring to FIG. 6, a three-dimensional brain image 600 generated from the brain MRI image of the object is shown.

Furthermore, an example of generating the segmented three-dimensional brain image 610 of the object from a segmented two-dimensional brain MRI image of the object is shown in FIG. 6.

In operation S140, the computer may generate a three-dimensional brain map of the object, which is capable of simulating a process of delivering electrical stimulation to the brain of the object, based on properties of each of the plurality of regions included in the three-dimensional brain image generated in operation S130.

A detailed method of generating the three-dimensional brain map of the object and performing simulation using the generated brain map will be described below with reference to FIG. 2.

Figure 2:
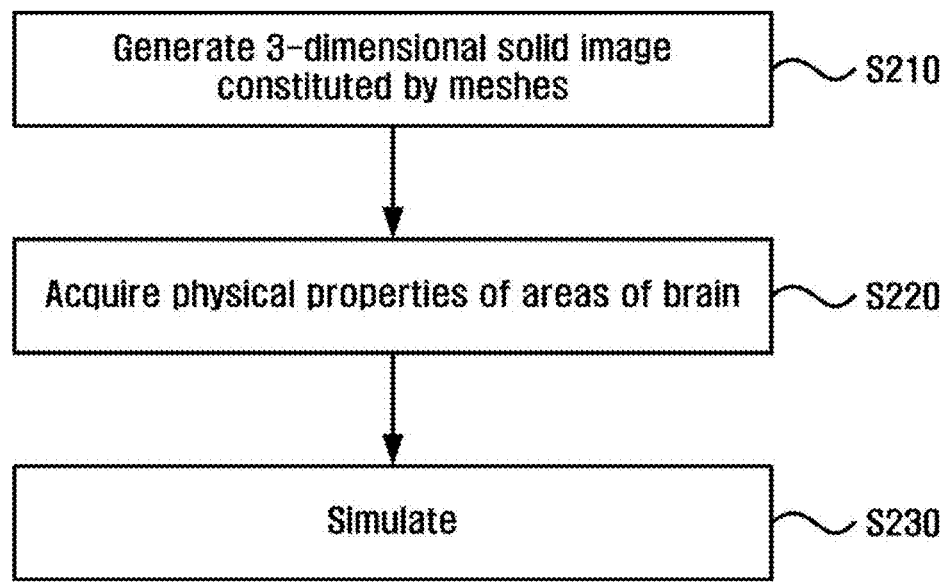
FIG. 2 is a flowchart illustrating a method for generating a three-dimensional brain map of an object and performing simulation according to an embodiment.
Figure 7:
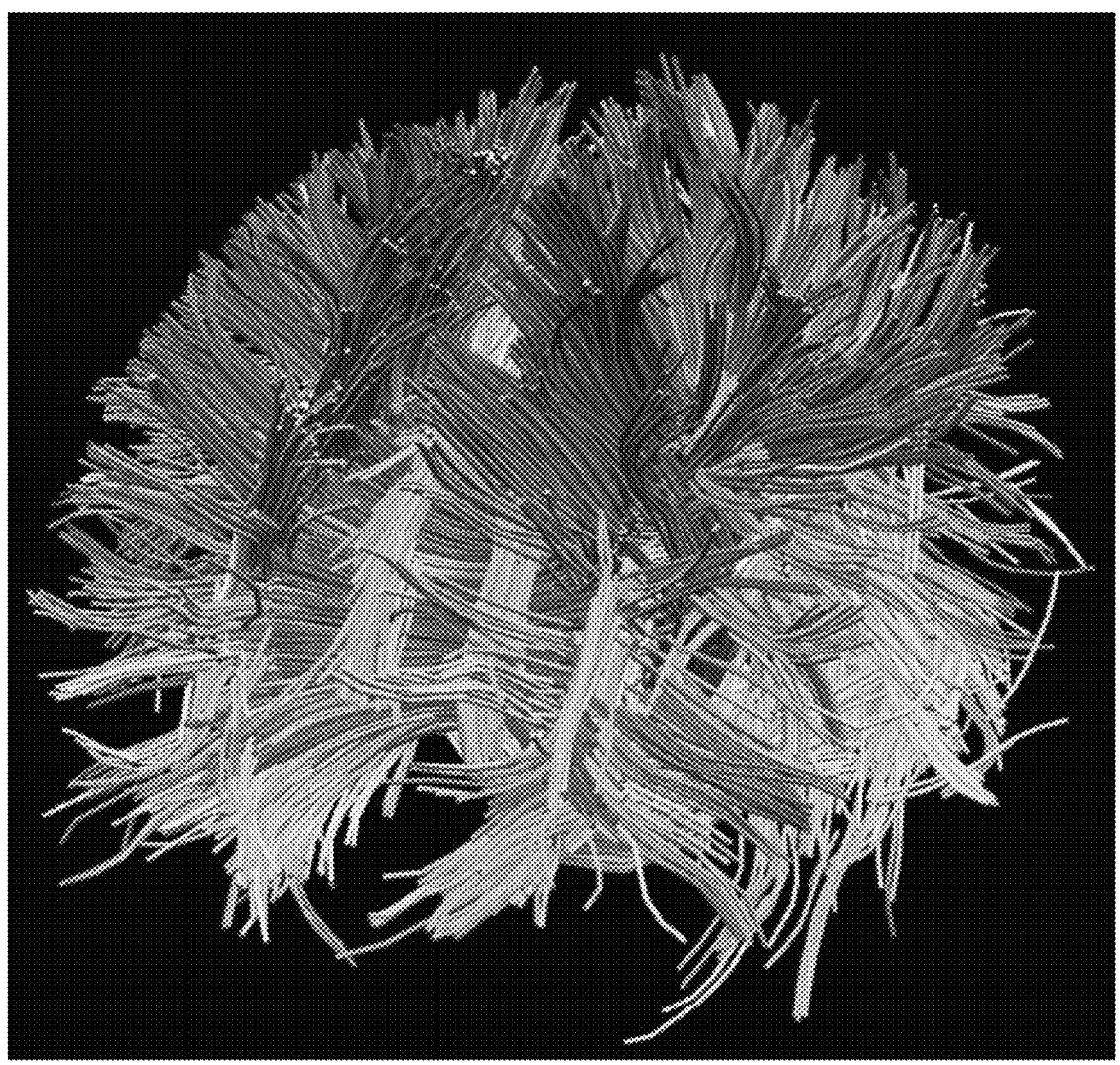
FIG. 7 is a drawing illustrating an example of a diffusion tensor image.
Figure 8:
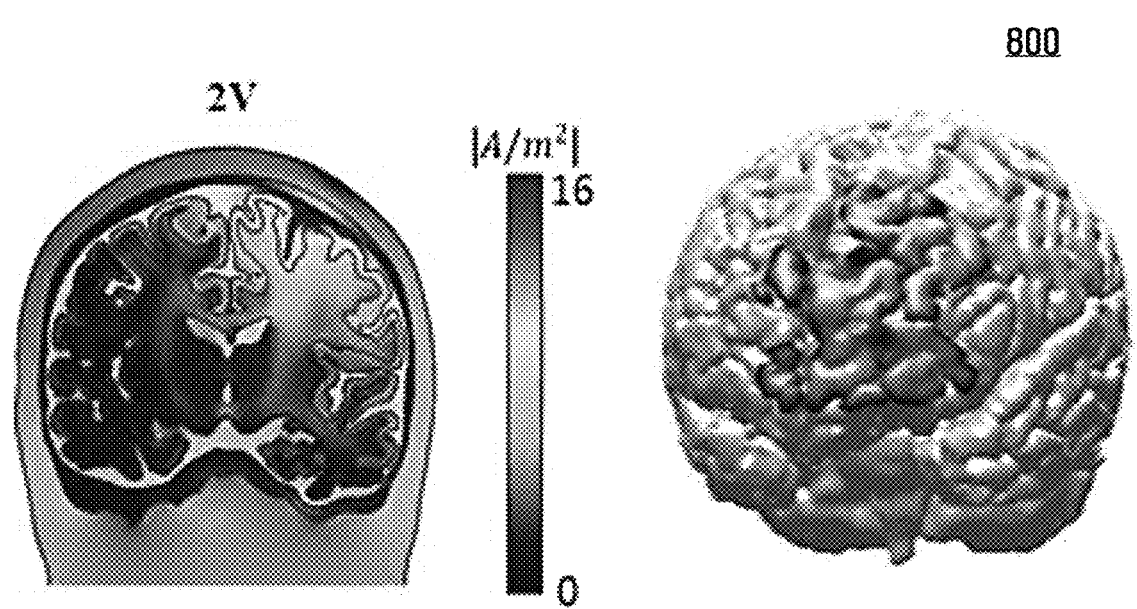
FIG. 8 is a drawing illustrating an example of a simulation result.

FIG. 2 is a flowchart illustrating a method for generating a three-dimensional brain map of an object and performing simulation according to an embodiment. FIG. 7 is a drawing illustrating an example of a diffusion tensor image. FIG. 8 is a drawing illustrating an example of a simulation result.

The method shown in FIG. 2 may correspond to an embodiment of a method shown in FIG. 1. Thus, although there are contents omitted in conjunction with FIG. 2, contents described in conjunction with FIG. 1 are also applied to the method shown in FIG. 2.

In operation S210, a computer may generate a three-dimensional stereoscopic image composed of a plurality of meshes, which is capable of simulating a process of delivering electrical stimulation to the brain of an object, using a three-dimensional brain image of an object.

In an embodiment, the computer may generate a three-dimensional stereoscopic image composed of a plurality of surface meshes, each of which includes triangles or quadrangles.

In an embodiment, the computer may generate a three-dimensional stereoscopic image composed of a plurality of volumetric meshes, each of which includes tetrahedrons or hexahedrons.

Types of the meshes constituting the three-dimensional stereoscopic image may be differently set according to a purpose of simulation.

In operation S220, the computer may acquire a physical characteristic of each of the plurality of regions for simulating a flow of current according to electrical stimulation to the brain of the object.

In an embodiment, the physical characteristic acquired in obtained S220 may include at least one of isotropic electrical conductivity and anisotropic electrical conductivity of each of the plurality of segmented regions.

In an embodiment, the isotropic electrical conductivity may be acquired by assigning electrical conductivity known by an experiment to each segmented region.

For example, electrical conductivity known for each region of the brain is shown in Table 1 below.

TABLE 1

| Region | Electrical conductivity (S/m) |
| --- | --- |
| White matter | 0.126 |
| Gray matter | 0.276 |
| Cerebrospinal fluid | 1.65 |
| Skull | 0.01 |
| Skin | 0.465 |

The anisotropic electrical conductivity may implement anisotropy of white matter fibers in the white matter of the brain.

In an embodiment, the anisotropic electrical conductivity may be acquired from a conductivity tensor image for the brain of the object.

For example, the computer may acquire a conductivity tensor image for the brain of the object from the brain MRI image of the object and may acquire anisotropic electrical conductivity of each of the plurality of segmented regions using the acquired conductivity tensor image.

In another embodiment, the brain MRI image of the object may include a diffusion tensor image, and the computer may acquire anisotropic electrical conductivity of each of the plurality of segmented regions using the acquired diffusion tensor image.

Referring to FIG. 7, an example of a diffusion tensor image 700 is shown.

It is known that an eigenvector of the diffusion tensor image is identical to an eigenvector of the conductivity tensor. The computer may acquire anisotropic electrical conductivity in the direction of a neural fiber included in the diffusion tensor image. For example, the direction of the neural fiber may have high electrical conductivity, and a direction perpendicular to the neural fiber may have low electrical conductivity.

When specific electrical stimulation is applied to one point of the head of the object using the three-dimensional brain map, in operation S230, the computer may simulate a state where the specific electrical stimulation is propagated in the brain of the object.

In an embodiment, the computer may simulate the state where the electrical stimulation is propagated in the brain of the object using the mesh image acquired in operation S210 and the physical characteristic acquired in operation S220.

Referring to FIG. 8, an example of the simulation result is shown.

The electrical stimulation capable of being applied to the head of the object may include at least one of a magnetic field, an electric field, and current. When a magnetic field is applied to the head of the object, current induced by the magnetic field may be propagated in the brain of the object.

In an embodiment, the computer may acquire a stimulation target point to apply electrical stimulation on the brain of the object. The computer may acquire a position to apply electrical stimulation to the head of the object to apply the electrical stimulation to the stimulation target point, using the three-dimensional brain map of the object.

For example, the computer may acquire a recommended path for delivering electrical stimulation from the scalp of the object and the stimulation target point, using the three-dimensional brain map of the object and may acquire a position to apply electrical stimulation to the head of the object from the recommended path.

The method for calculating and providing the position and direction to apply the electrical stimulation to the brain of the object will be described below.

Figure 9:
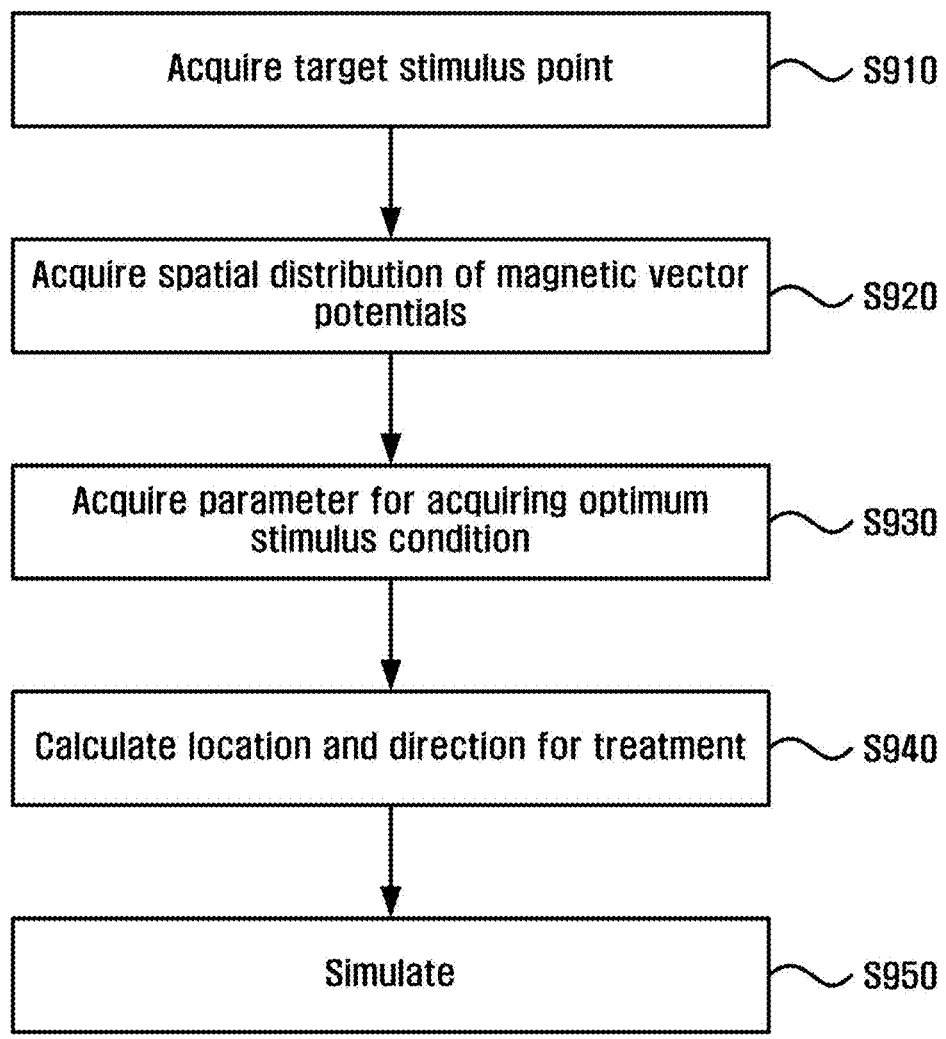
FIG. 9 is a flowchart illustrating a TMS stimulation navigation method according to an embodiment.
Figure 10:
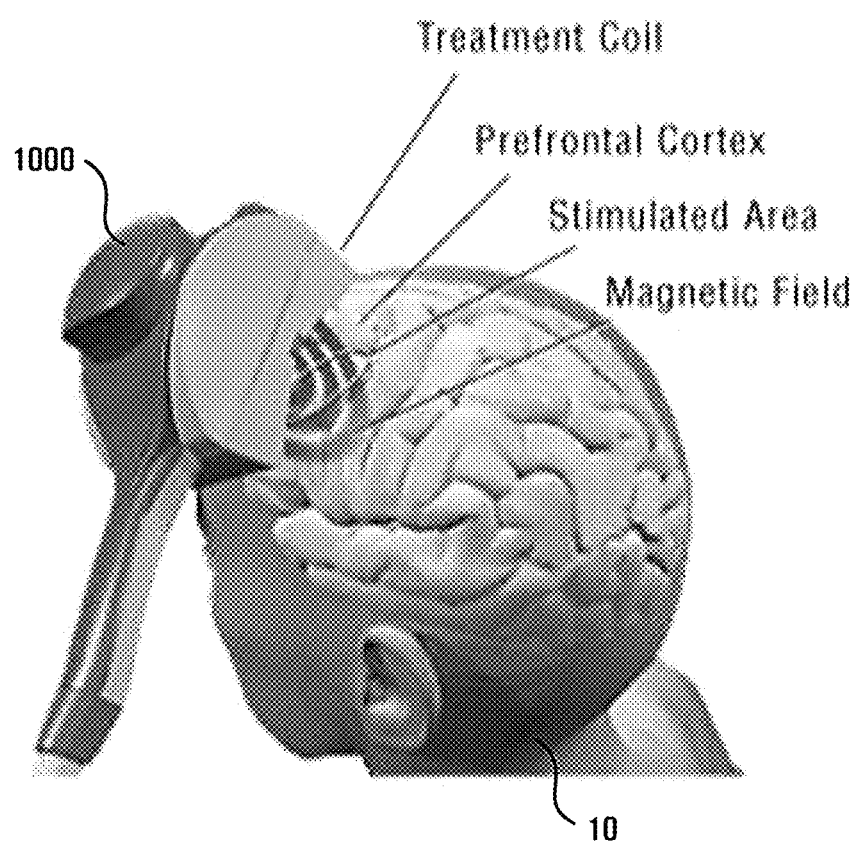
FIG. 10 is a drawing illustrating an example of a TMS procedure method according to an embodiment.
Figure 11A:
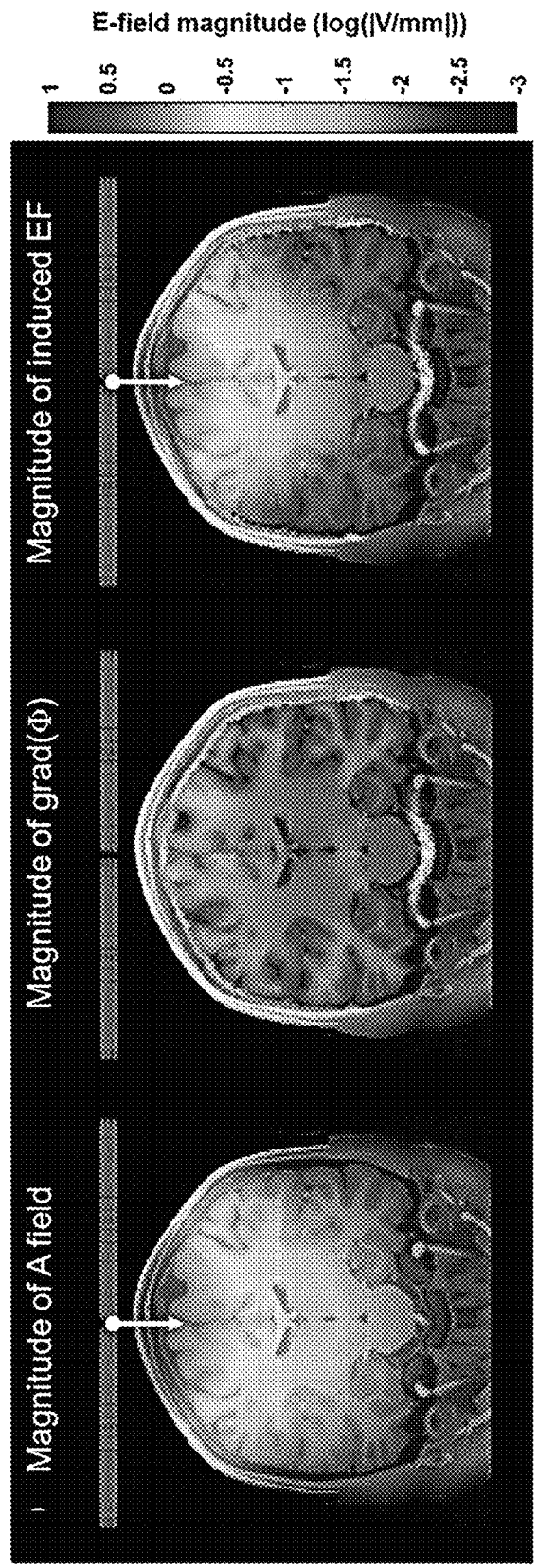
FIGS. 11A and 11B are drawings illustrating a relationship between a magnetic field and an electric field applied to a brain of an object.
Figure 11B:
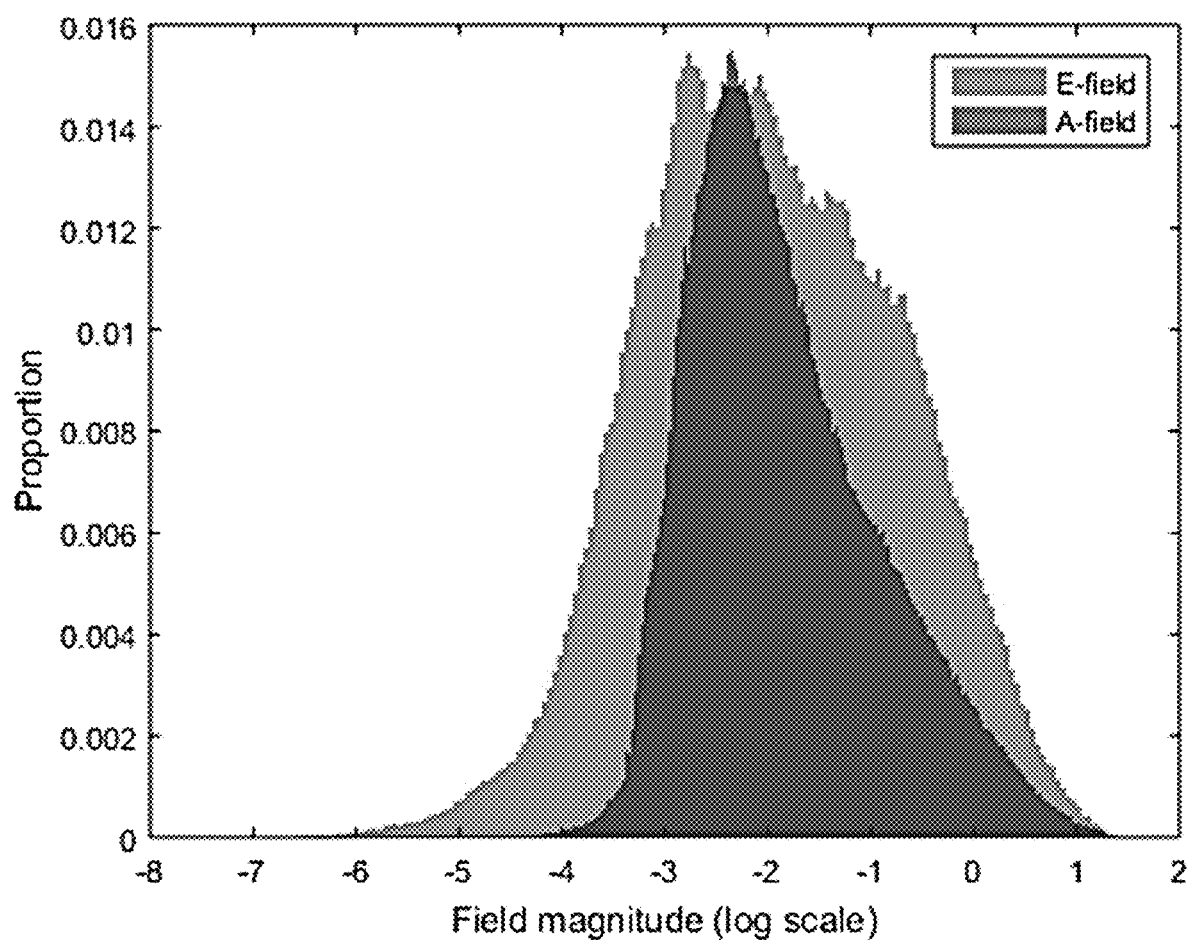
Figure 12:
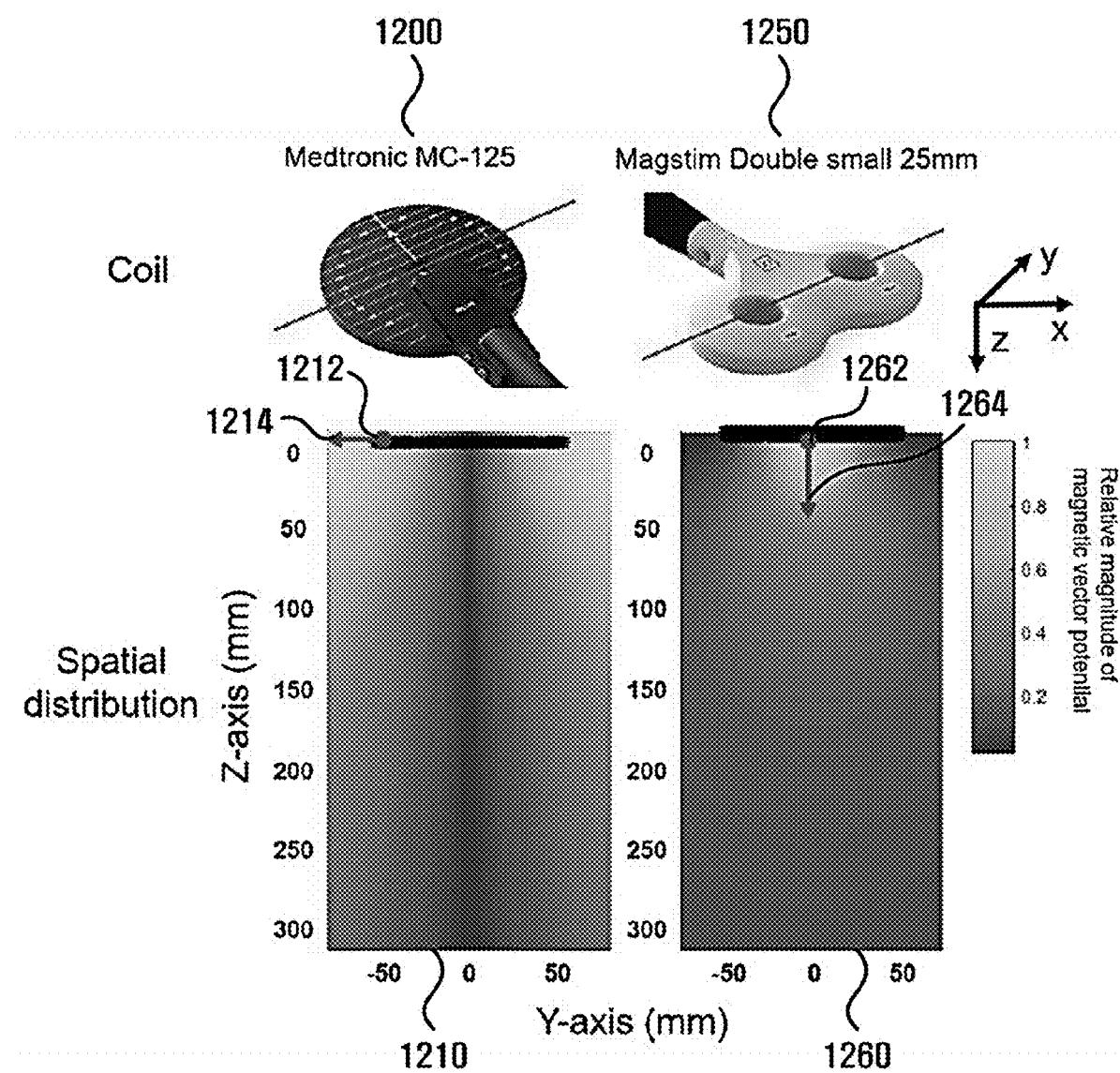
FIG. 12 is a drawing illustrating information visualizing a magnetic vector potential according to a type of a coil for procedure.
Figure 13:
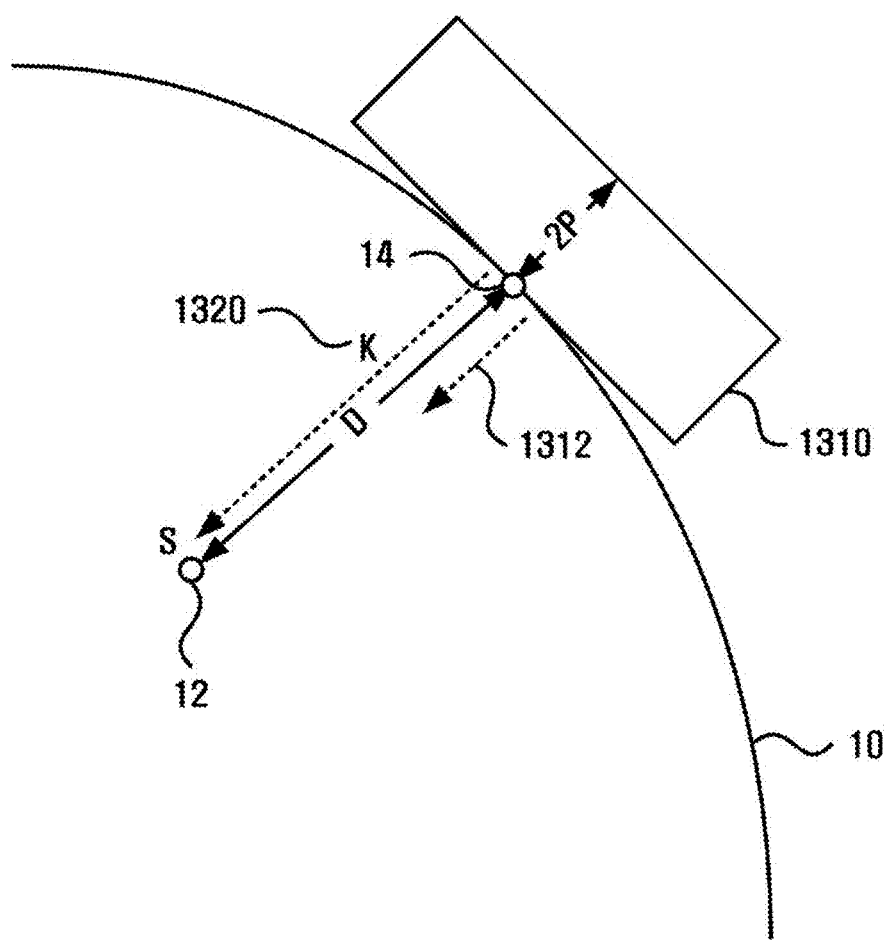
FIG. 13 is a drawing illustrating an example of a method for calculating a position and direction of a coil.
Figure 14:
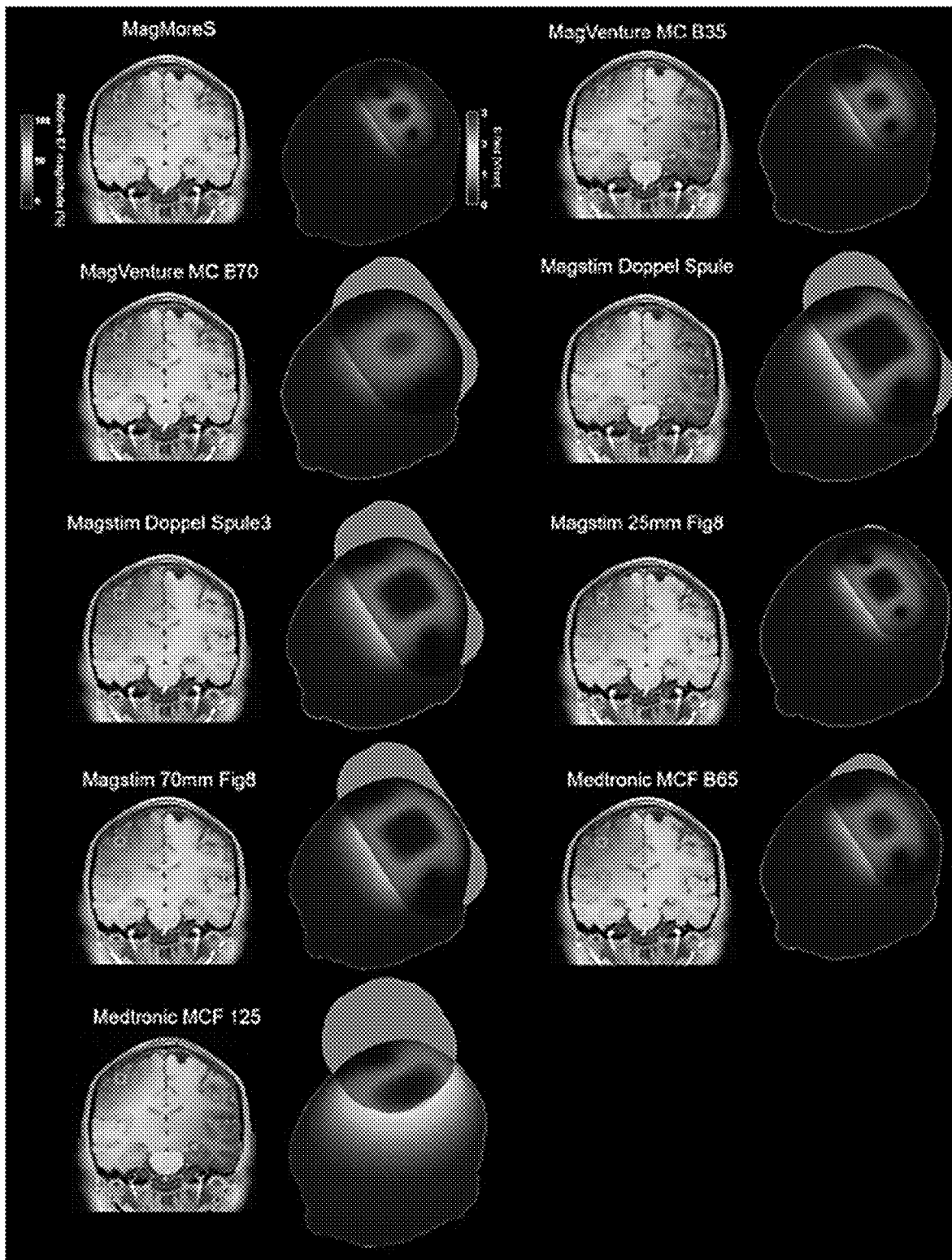
FIG. 14 is a drawing illustrating examples of visualizing a state where electrical stimulation induced from a magnetic field of a coil for procedure is propagated in the brain of an object.

FIG. 9 is a flowchart illustrating a transcranial magnetic stimulation (TMS) stimulation navigation method according to an embodiment. FIG. 10 is a drawing illustrating an example of a TMS procedure method according to an embodiment. FIGS. 11A and 11B are drawings illustrating a relationship between a magnetic field and an electric field applied to a brain of an object. FIG. 12 is a drawing illustrating information visualizing the magnetic vector potential according to a type of a coil for procedure. FIG. 13 is a drawing illustrating an example of a method for calculating a position and direction of a coil. FIG. 14 is a drawing illustrating examples of visualizing a state where electrical stimulation induced from a magnetic field of a coil for procedure is propagated in a brain of an object.

The TMS stimulation navigation method shown in FIG. 9 shows operations, performed by a computer, in time series.

Referring to FIG. 10, an example of the TMS procedure method is shown.

TMS is a treatment method of making a treatment coil 1000 close to one side of the head of an object 10 and stimulating a specific portion of the brain using an electric field induced in the brain of the object 10 by a magnetic field generated by the coil 1000.

A magnetic field generated around the treatment coil 1000 may vary in intensity and shape according to a shape of the treatment coil 1000. An appearance in which an electrical signal is propagated may also vary according to a shape of the head and brain of the object 10.

Thus, according to the disclosed embodiment, the computer may calculate and provide a stimulation point according to a type of the coil 1000 and may provide a simulation result according to the shape of the head and brain of the object 10.

In operation S910, the computer may acquire a stimulation target point to apply electrical stimulation on the brain of the object.

The stimulation target point may be selected on a clinical or theoretical basis according to disease to be treated. In an embodiment, the stimulation target point be indicated using the three-dimensional brain image or the three-dimensional brain map of the object generated by the disclosed embodiment.

In operation S920, the computer may acquire information about a spatial distribution of a magnetic vector potential of a coil for TMS procedure.

In an embodiment, the information about the spatial distribution may include information visualizing the magnetic vector potential using a magnetic dipole according to a shape of the coil for TMS procedure.

Referring to FIG. 12, information 1210 and 1260 visualizing magnetic vector potentials according to types of coils 1200 and 1250 for procedure is shown.

In operation S930, the computer may acquire one or more parameters for acquiring an optimal stimulation condition for the stimulation target point acquired in operation S910, from the spatial distribution acquired in operation S920.

In an embodiment, the optimal stimulation condition for the stimulation target point may refer to a condition where an intensity of a magnetic field applied to the stimulation target point by the coil for TMS procedure becomes maximum.

Referring to FIGS. 11A and 11B, a relationship between a magnetic field and an electric field applied to the brain of the object is shown.

Referring to a simulation image 1100 of FIG. 11A, images acquired by respectively visualizing a magnitude of a magnetic field applied to the brain of the object, a magnitude of a gradient (potential), and a magnitude of an electric field induced by the magnetic field are shown. The magnitude of the electric field applied to the brain of the object may be calculated by adding the magnetic field applied to the brain of the object and the gradient.

Referring to a graph of FIG. 11B, a correlation between the magnetic field applied to the brain of the object and the electric field induced by the magnetic field is shown.

According to the graph of FIG. 11B, it may be seen that, as a stronger magnetic field is applied to the brain of the object, a stronger electric field is induced in the brain of the object.

Thus, it may be seen that the maximum stimulation condition for the stimulation target point is a condition where the intensity of the magnetic field applied to the stimulation target point by the coil for procedure becomes maximum.

In an embodiment, the parameter acquired by the computer may include an optimal point having the highest magnetic vector potential value in the spatial distribution of the magnetic vector potential induced by the coil.

Furthermore, the parameter acquired by the computer may include an optimal vector which is a normal vector where multiplication with a gradient at the optimal point becomes minimum among normal vectors where the optimal point is a start point.

Referring to FIG. 12, optimal points 1212 and 1262 and optimal vectors 1214 and 1264 of the magnetic vector potentials 1210 and 1250 are shown.

An optimal point (x, y, z) and an optimal vector v may be calculated by Equations 1 and 2 below.

$$\max_{x,y,z} f(x, y, z) \quad \text{[Equation 1]}$$

In Equation 1 above, f denotes the magnetic vector potential map. A position (x, y, z) having the highest value in the magnetic vector potential map f may be calculated as an optimal point by Equation 1 above.

$$\min_{x,y,z} \nabla f(x, y, z)^T v(x, y, z) \quad \text{[Equation 2]}$$

In Equation 2 above, $\nabla f(\bar{x}, \bar{y}, \bar{z})$ denotes the value acquired by differentiating f used when defining the optimal point at the optimal point $\bar{x}, \bar{y}, \bar{z}$, and v(x, y, z) denotes the normal vector in the direction of (x, y, z).

In step S940, the computer may calculate a position and direction of the coil, which satisfy the optimal stimulation condition for the stimulation target point acquired in operation S910, using the parameter acquired in operation S930.

In an embodiment, the calculating of the position and direction of the coil may include calculating the position and direction of the coil such that the stimulation target point is closest in the direction of the optimal vector from the optical point.

Referring to FIG. 13, an example of the method for calculating the position and direction of the coil is shown.

When an object 10 and a stimulation target point S 12 of the object 10 are acquired, the computer may determine one point 14 on the scalp closest from the stimulation target point 12.

In this case, a distance between the stimulation target point 12 and the one point 14 on the scalp closest from the stimulation target point 12 is D, and a vector where the point 14 is a start point and where the stimulation target point 12 is an end point is K. Furthermore, a thickness of a coil 1310 is 2P.

The computer may generate and apply a matrix, shown in Equation 3 below, arranging a vector K 1320 and an optimal vector 1312 of the coil 1310.

$$R_x(\theta) = \begin{bmatrix} 1 & 0 & 0 \\ 0 & \cos\theta & -\sin\theta \\ 0 & \sin\theta & \cos\theta \end{bmatrix} \quad \text{[Equation 3]}$$

$$R_y(\theta) = \begin{bmatrix} \cos\theta & 0 & \sin\theta \\ 0 & 1 & 0 \\ -\sin\theta & 0 & \cos\theta \end{bmatrix}$$

$$R_z(\theta) = \begin{bmatrix} \cos\theta & -\sin\theta & 0 \\ \sin\theta & \cos\theta & 0 \\ 0 & 0 & 1 \end{bmatrix}$$

Thus, the location of the coil may be calculated as Equation 4 below.

$$\text{Loc}_{dipole} = S + K*(D+P) \quad \text{[Equation 4]}$$

In operation S950, when placing the coil for procedure at the location calculated in operation S940 in the direction calculated in operation S940, the computer may simulate a state where electrical stimulation induced from a magnetic field of the coil for procedure is propagated in the brain of the object.

In an embodiment, the computer may perform simulation using the three-dimensional brain map generated according to in the method shown in FIGS. 1 and 2.

For example, the computer may acquire a brain MRI image of the object and may generate the three-dimensional brain map of the object, which is capable of simulating a process of delivering electrical stimulation to the brain of the object, based on properties of each of a plurality of regions included in the acquired brain MRI image.

The computer may simulate a state where electrical stimulation by the coil is propagated in the brain of the object, using the generated three-dimensional brain map.

Furthermore, the three-dimensional brain map may include a three-dimensional stereoscopic image composed of a plurality of meshes, which is capable of simulating a process of delivering electrical stimulation to the brain of the object.

In an embodiment, the computer may visualize a state where electrical stimulation induced from a magnetic field of the coil for procedure is propagated in the brain of the object, using the three-dimensional stereoscopic image.

Referring to FIG. 14, examples of visualizing a state where electrical stimulation induced from a magnetic field of the coil for procedure is propagated in the brain of the object are shown.

In the disclosed embodiment, the computer may be connected with a robot arm device equipped with a coil for TMS procedure. The robot arm device may include a mechanical device capable of moving the coil for TMS procedure to a position specified by the computer.

The robot arm device may automatically perform a procedure using the TMS coil for a patient depending on the result calculated by the computer by moving the coil for TMS procedure to the position specified by the computer according to the disclosed embodiment.

Figure 15:
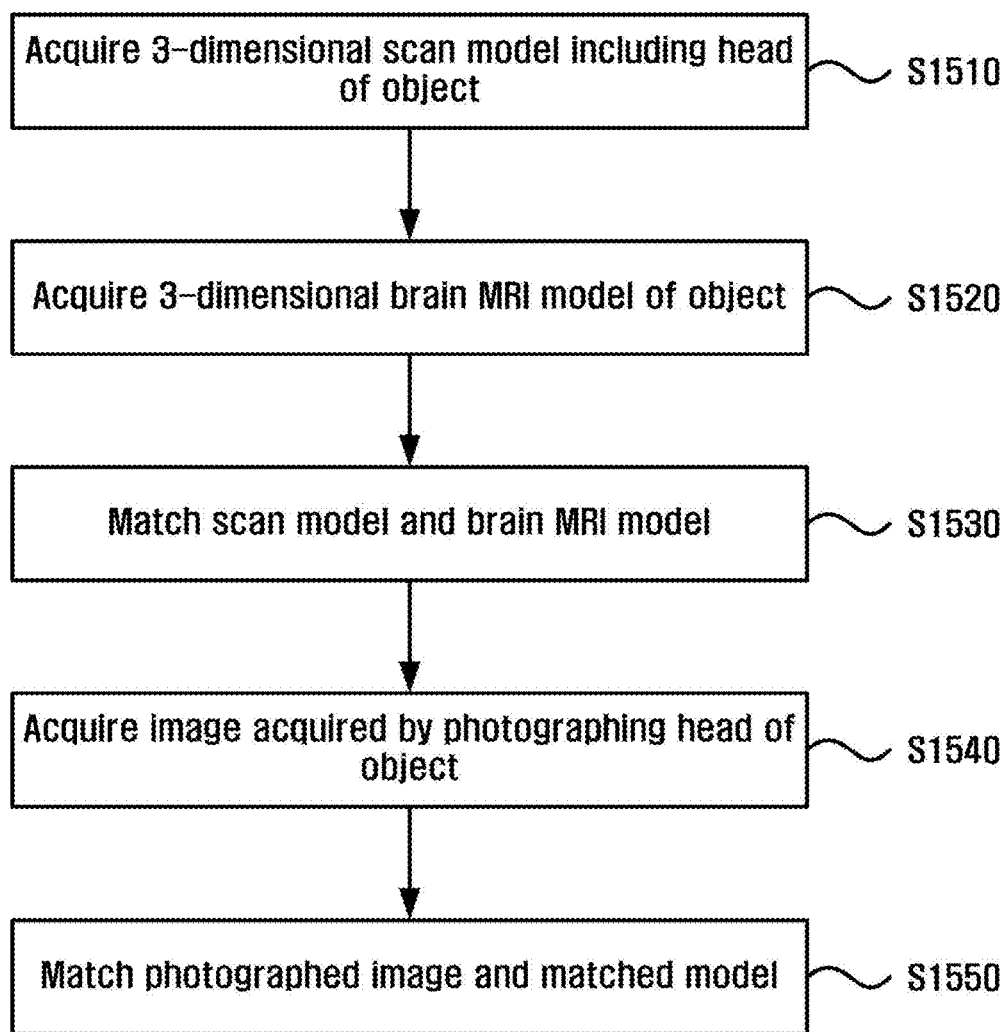
FIG. 15 is a flowchart illustrating a patch guide method according to an embodiment.
Figure 17:
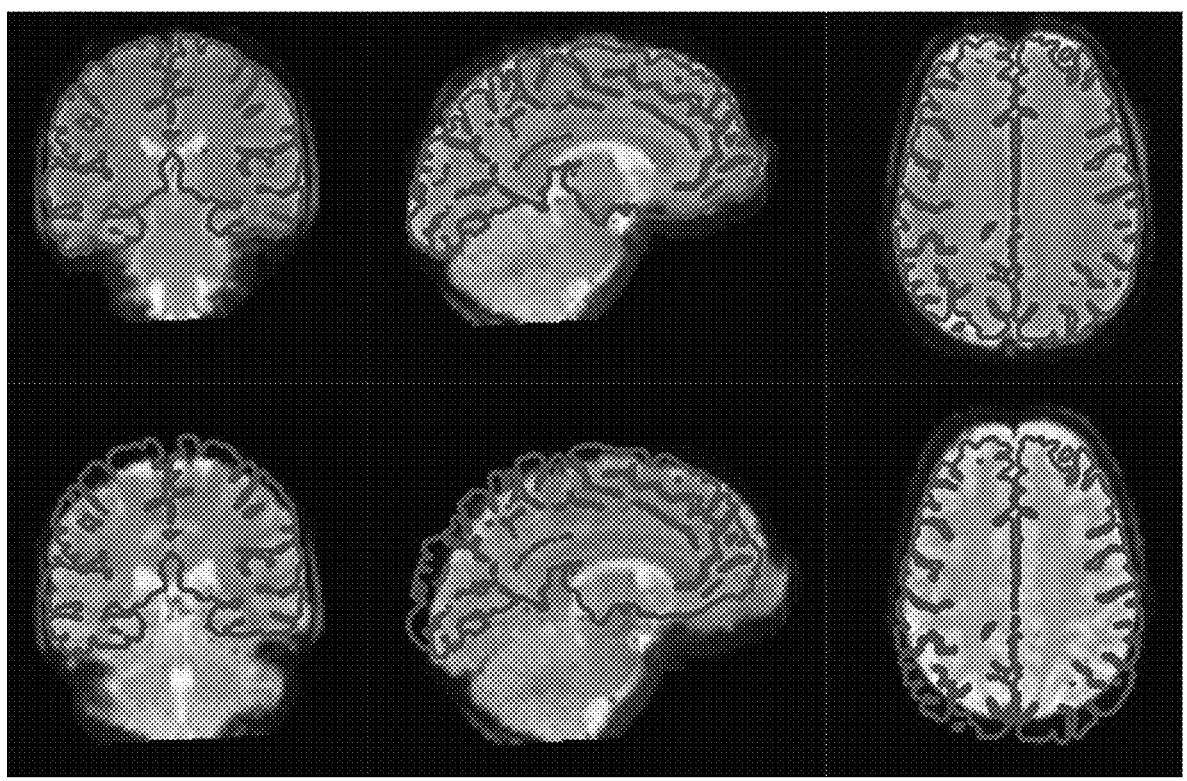
FIG. 17 is a drawing illustrating an embodiment of a method for matching images.
Figure 18:
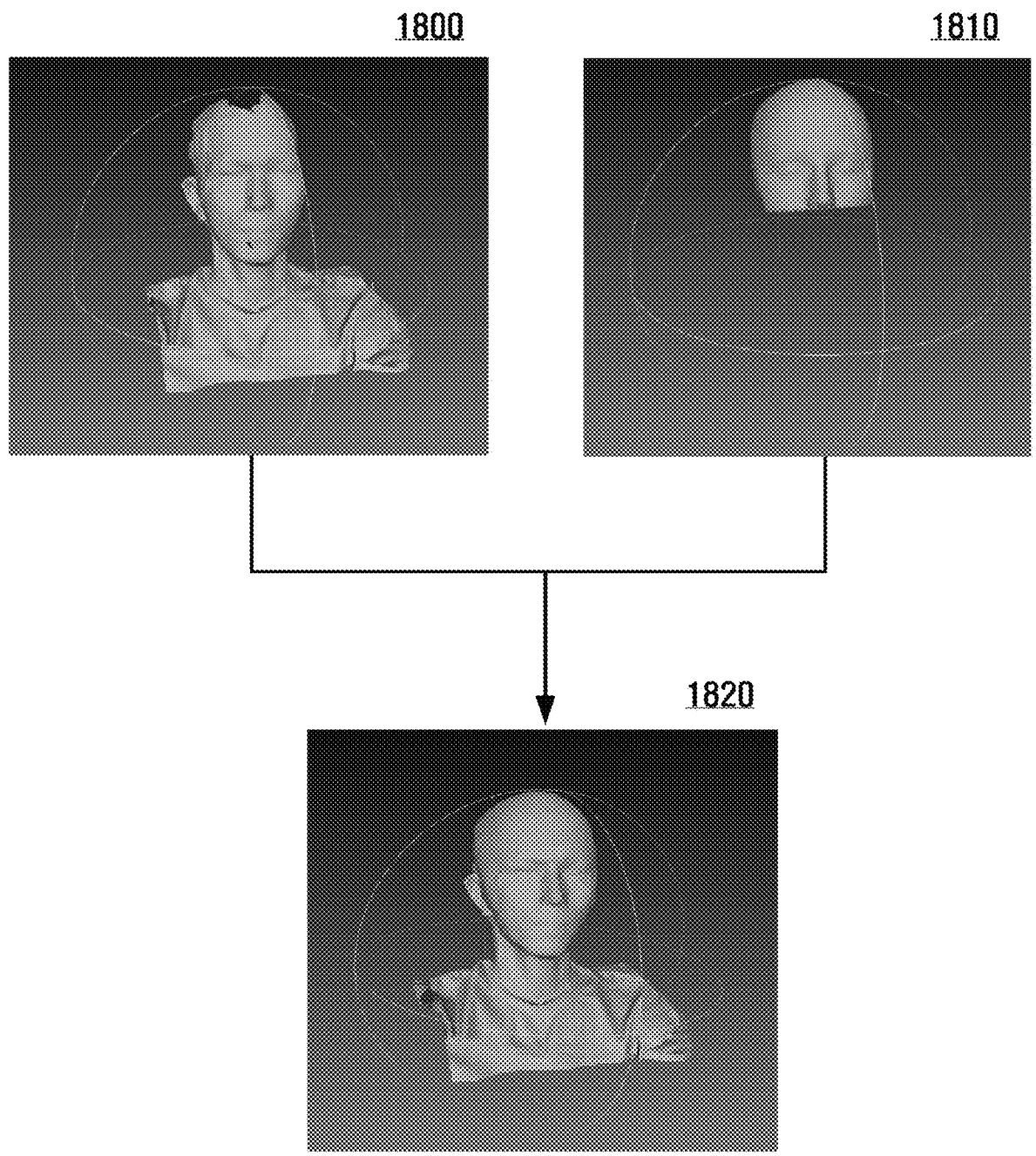
FIG. 18 is a drawing illustrating an example of a three-dimensional scan model obtained using a depth camera.
Figure 19:
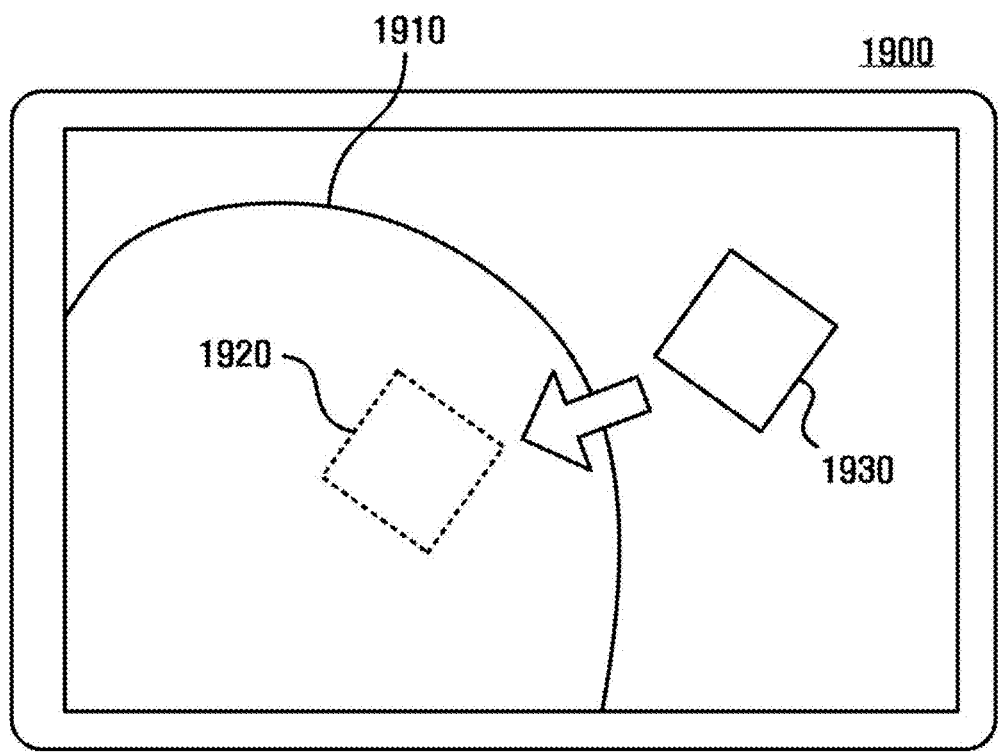
FIG. 19 is a drawing illustrating an example in which a computing device connected with a depth camera module captures the head of an object and guides a doctor to a position for attaching a patch to the captured head of the object.
Figure 20:
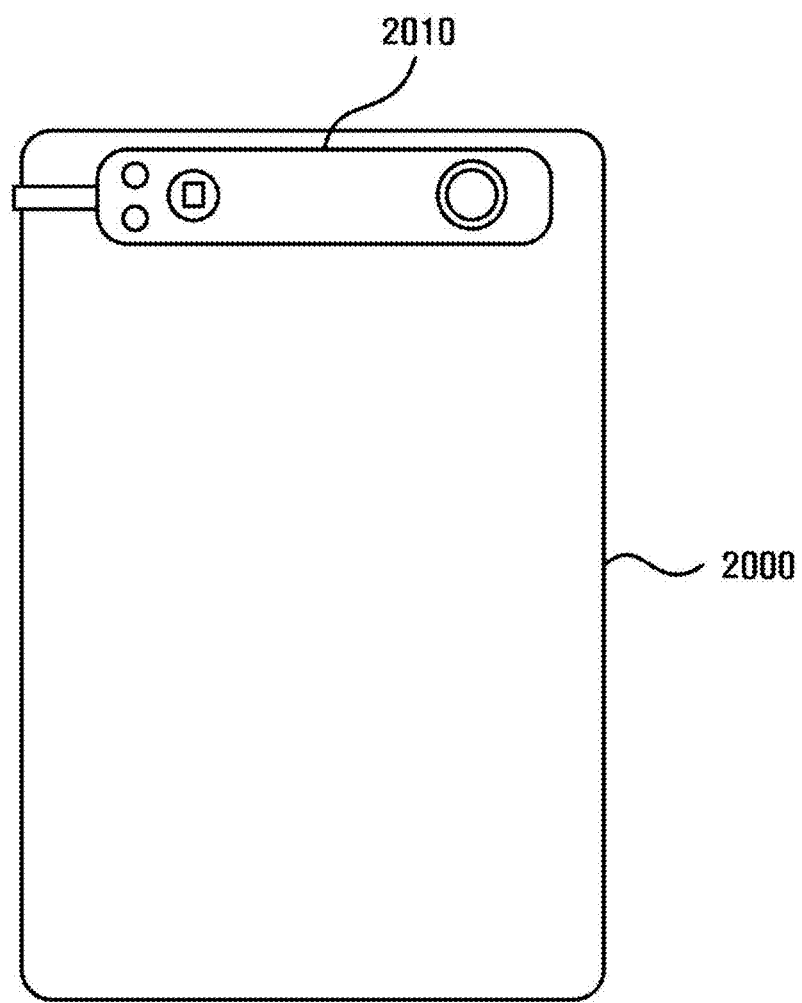
FIG. 20 is a drawing illustrating a portable computing device and a depth camera module connected thereto.

FIG. 15 is a flowchart illustrating a patch guide method according to an embodiment. FIG. 17 is a drawing illustrating an embodiment of a method for matching images. FIG. 18 is a drawing illustrating an example of a three-dimensional scan model acquired using a depth camera. FIG. 19 is a drawing illustrating an example in which a computing device connected with a depth camera module captures a head of an object and guides a location for attaching a patch to the captured head of the object. FIG. 20 is a drawing illustrating a portable computing device and a depth camera module connected thereto.

In the disclosed embodiment, a patch may include a brain stimulation patch. For example, the brain stimulation patch may include, but is not limited to, an electrical stimulation patch and an ultrasonic stimulation patch. Furthermore, the patch may include an EEG patch. Herein, the type of the patch according to the disclosed embodiment is not limited to the above-mentioned examples.

In operation S1510, a computer may acquire a three-dimensional scan model including the head of an object using a depth camera.

The depth camera may include a 3-dimensional laser scanner of a triangulation technique, a depth camera using a structure beam pattern, a depth camera using a time-of-flight (TOF) technique using a reflection time difference of an infrared ray, and the like, but the type thereof is not limited thereto.

The depth camera may be used to acquire a 3-dimensional scan model by reflecting distance information in an image.

In an embodiment, an object, that is, a patient sits on a round stool, and a user, that is, a doctor locates the depth camera using a temporary fixing device, such as, a tripod, such that the face of the patient is viewed well from a height of the face of the patient.

The doctor starts a scan using the depth camera, and acquires a 3-dimensional scan model including the head of the patient by turning the patient slowly one turn.

In an embodiment, the depth camera may be provided in a fixing module, which is automatically rotatable, and may rotate around the patient located in the center to acquire a 3-dimensional scan model.

Meanwhile, according to the disclosed embodiment, to facilitate a 3-dimensional scan without separate high-priced equipment, a depth camera module may be connected to a portable computing device (e.g., a smartphone, a tablet PC, or the like), the computing device, to which the depth camera module is connected, may be fixed using a temporary fixing device, such as a tripod, which may be easily acquired, and the patient may be rotated after he or she sits on a stool or the like to acquire a 3-dimensional scan model.

Referring to FIG. 20, a portable computing device 2000 and a depth camera module 2010 connected to the portable computing device 2000 are shown.

Furthermore, referring to FIG. 18, an example of a 3-dimensional scan model 1800 acquired using a depth camera is shown.

In an embodiment, the computer may generate a 3-dimensional model including the head of the object using a distance image collected using the depth camera, and may align and add images captured at different time points to reconstruct a 3-dimensional model of the object. For example, the computer may reconstruct a model by collecting 3-dimensional data in the form of a point cloud from distance images collected using the depth camera. However, the method for generating the 3-dimensional model is not limited.

In operation S1520, the computer may acquire a 3-dimensional brain MRI model of the object.

In an embodiment, the acquiring of the 3-dimensional brain MRI model of the object may include acquiring a brain MRI image of the object and generating a 3-dimensional brain map of the object, which is capable of simulating a process of delivering electrical stimulation to the brain of the object, based on properties of each of a plurality of regions included in the brain MRI Image of the object.

Moreover, the generating of the 3-dimensional brain map of the object may include generating a 3-dimensional stereoscopic image composed of a plurality of meshes, which is capable of simulating the process of delivering the electrical stimulation to the brain of the object.

The method for generating the 3-dimensional brain map, described in conjunction with FIGS. 1 to 8, may be used as the method for acquiring the 3-dimensional brain MRI model of the object by the computer in operation S1520.

In operation S1530, the computer may match the 3-dimensional scan model including the head of the object and the brain MRI model of the object.

Referring to FIG. 17, an embodiment of matching images is shown. Referring to an image 1700 shown in FIG. 17, a brain MRI picture of the object and an image acquired by modeling a brain structure of the object are overlapped with each other.

In the image 1700, the lower three images may correspond to an example in which the brain MRI picture and the image acquired by modeling the brain structure are not matched with each other. Furthermore, in the image 1700, the upper three images may correspond to an example in which the brain MRI picture and the image acquired by modeling the brain structure are matched with each other.

The computer may calculate a change generated in the brain of the object by electrical or ultrasonic stimulation of a patch depending on a location at which the patch is attached, using the brain MRI model. Furthermore, the computer may calculate a location to actually attach the patch, using the 3-dimensional scan model including the head of the object.

Thus, the computer may calculate a location to attach the patch to the head of the object by matching the 3-dimensional scan model including the head of the object and the brain MRI model of the object, and may thus calculate a change generated in the brain of the object. Similarly, the computer may calculate a location to attach the patch to the head of the object to cause a specific change in the brain of the object and may provide the result.

In an embodiment, the matching by the computer may include calculating facial features of the scan model and the brain MRI model and matching the scan model and the brain MRI model using the facial features of the scan model and of the brain MRI model.

Because the scan model including the head of the object and the brain MRI model of the object differ in style from each other, it is difficult to match the two models. Thus, the computer may match the two models using the facial feature of the object.

In an embodiment, the calculating of the facial feature of the scan model including the head of the object may include acquiring a color image and a depth image, each of which includes the head of the object, calculating the facial feature of the object using the color image including the head of the object, and calculating a 3-dimensional location of the facial feature of the object using the depth image including the head of the object.

Referring to FIG. 18, an example of matching the scan model 1800 including the head of the object and a brain MRI model 1810 of the object to generate the matched model 1820 is shown.

In operation S1540, the computer may acquire an image by capturing the head of the object using the depth camera.

For example, the doctor may move while directly carrying the temporarily fixed depth camera such that the depth camera faces the head of the patient.

In operation S1550, the computer may match one location of the image captured in operation S1540 and one location on the matched model.

For example, when the computer captures one point of the head of the object using the depth camera, it may calculate where the one point being captured corresponds to on the matched model.

In an embodiment, the computer may match the captured image and the matched model and may display an image for guiding a user to the location of the patch to be attached to the head of the object.

Referring to FIG. 19, a computing device 1900, to which a depth camera module is connected, may capture a head 1910 of the object. The computing device 1900 may display an image for guiding a user to a location 1920 for attaching a patch 1930 to the captured head 1910 of the object.

In an embodiment, the computing device 1900 may determine a location to attach the patch 1930 on the matched model and may display the location 1920 corresponding to the location determined on the captured image.

Furthermore, the computing device 1900 may recognize the patch 1930 on the captured image and may guide a user along a movement direction of the recognized patch 1930.

Furthermore, the computing device 1900 may determine whether the recognized patch 1930 is attached to the determined location 1920.

In an embodiment, at least one marker is attached to or displayed on the patch 1930. For example, at least one of a specific figure, a specific color, and a specific 2-dimensional code may be attached to or displayed on the patch 1930, and the computing device 1900 may recognize the patch 1930 using the marker attached to or displayed on the patch 1930 and may track movement of the patch 1930.

For example, when the doctor captures the head of the patient using the computing device 1900 or the depth camera connected to the computing device 1900 while changing the location of the head, the location of the head of the patient displayed on the computing device 1900 may also be changed and the location of the patch 1930 recognized by the computing device 1900 may also be changed. In this case, the computing device 1900 may track the patch 1930 even when the computing device 1900 is moved to guide the doctor to attach the patch 1930 to an accurate location of the head of the patient.

In an embodiment, the computing device 1900 may recognize the patch 1930 on the captured image and may guide a user along a movement direction of the recognized patch 1930. For example, the computing device 1900 may display the movement direction of the patch 1930 such that the patch 1930 may be attached to the determined location 1920.

Furthermore, the computing device 1900 may determine whether the recognized patch 1930 is attached to the determined location 1920. For example, the computing device 1900 may determine whether a location where the patch 1930 is finally recognized corresponds to the determined location 1920. When the determined location 1920 and the location to which the patch 1930 is attached differ from each other, the computing device 1900 may provide a notification for requesting to change the location of the patch 1930.

In an embodiment, the computing device 1900 may recognize the patch 1930 attached to the head of the object on the captured image and may determine the location of the recognized patch 1930. The computing device 1900 may acquire a location on the matched model, which corresponds to the determined location of the patch 1930.

For example, when an EEG is performed, an EEG patch may be attached to a consistent location regardless of the shape and structure of the head of the user, or an EEG patch may be attached to any location. In this case, it is difficult to know in detail whether the brain wave acquired by the EEG patch is a brain wave received from any direction of the brain of the object.

Thus, according to the disclosed embodiment, the computing device 1900 may capture the head of the object, to which one or more EEG patches are attached, and may acquire the locations of the one or more recognized EEG patches from the captured image.

The computing device 1900 may acquire a location on the matched model of the object, corresponding to the acquired location of the EEG patch, and may determine in detail whether the brain wave acquired by the EEG patch attached to the head of the object is received from any portion of the brain of the object. For example, the computing device 1900 may analyze a signal source of the brain wave received from each EEG patch utilizing the disclosed embodiment.

Figure 16:
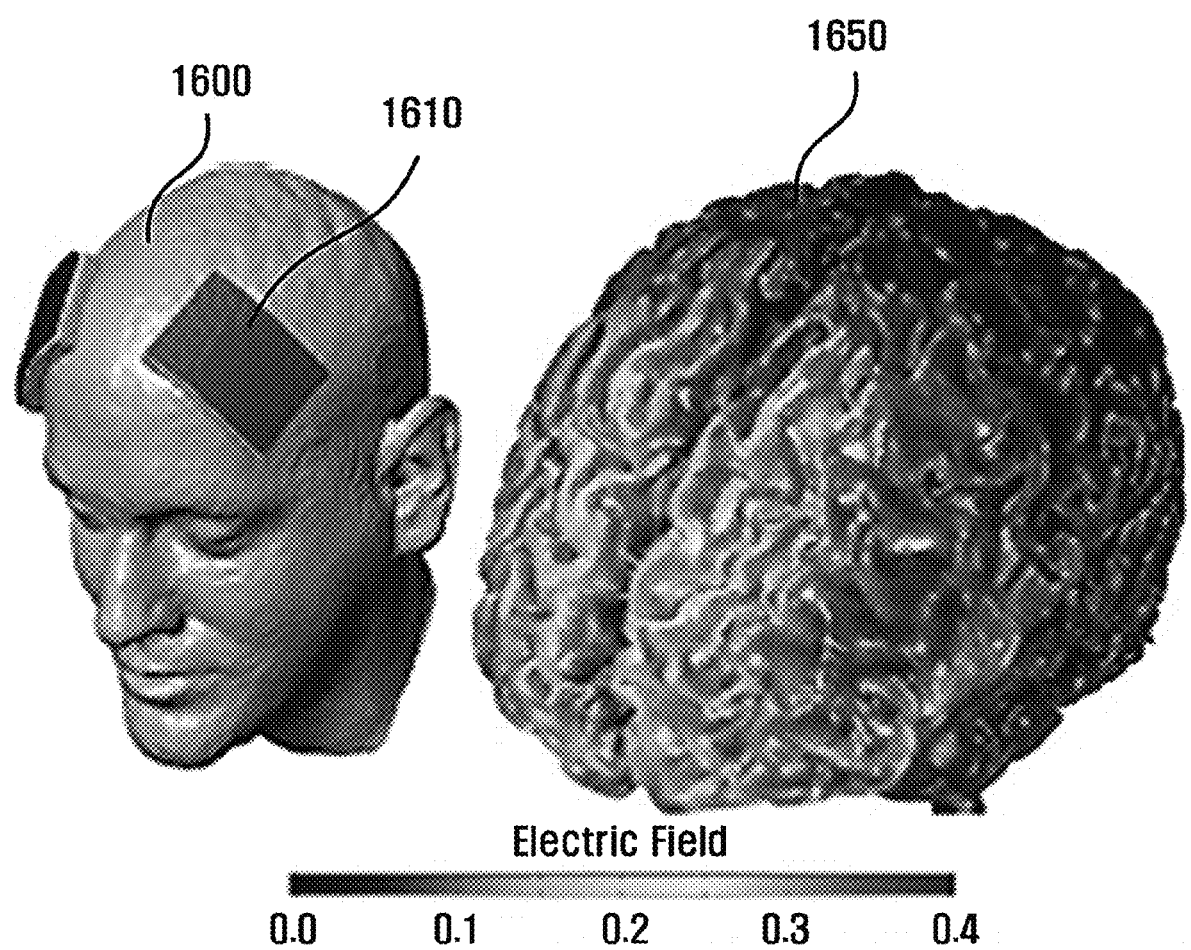
FIG. 16 is a drawing illustrating the result of simulating an electrical stimulation result according to an embodiment.

FIG. 16 is a drawing illustrating the result of simulating an electrical stimulation result according to an embodiment.

Referring to FIG. 16, a 3-dimensional model of a head 1600 of an object and an embodiment in which a patch 1610 is attached to one location on the 3-dimensional model are shown.

When the patch 1610 is attached to the one location of the 3-dimensional model of the head 1600 of the object, a computer may simulate the result of delivering electrical stimulation by the patch 1610 to the brain 1650 of the object.

In an embodiment, the computer may acquire a 3-dimensional brain map for the brain 1650 of the object and may determine a location of the patch 1610 to be attached to the head of the object, using the 3-dimensional brain map.

In an embodiment, the determining of the location of the patch 1610 may include acquiring a purpose of using the patch 1610, simulating a process of delivering electrical stimulation to the brain 1650 of the object depending on the location at which the patch 1610 is attached to the head 1600 of the object, and determining the location of the patch 1610 using the acquired purpose and the simulation result.

For example, when desiring to apply specific stimulation to the brain 1650 of the object, the computer may determine the location of the patch 1610 at which specific stimulation may be applied to the brain 1650 of the object, using the simulation result.

The computer may match the location of the patch 1610 determined according to the embodiment illustrated in FIG. 16 with one point of the head of the object captured using the depth camera and may display an image for guiding the patch to the matched location.

Steps of the method or algorithm described in connection with an embodiment of the inventive concept may be directly implemented in hardware, may be implemented with a software module executed by hardware, or may be implemented by a combination of the hardware and the software module. The software module may reside on a random access memory (RAM), a read only memory (ROM), an erasable programmable ROM (EPROM), an electrically erasable programmable ROM (EEPROM), a flash memory, a hard disc, a removable disc, a CD-ROM, or any type of computer-readable storage medium which is well known in the technical field to which the inventive concept pertains.

According to the disclosed embodiment, the computer may segment a brain MRI image using the previously learned model to segment the brain MRI image automatically within a short time.

Thus, anyone may acquire a three-dimensional brain image of the object within a short time in the medical field. In addition, the computer may provide a simulation effect capable of visually identifying the effect of electrical stimulation to the brain of the object.

Furthermore, the computer may calculate and provide a stimulation point capable of applying optimal stimulation to a stimulation target point by using magnetic vector potential information according to a type of a coil for TMS procedure together, thus increasing the effect of procedure.

Furthermore, the computer may guide the doctor to the location of an electrical stimulation path using head modeling and MRI modeling to guide the doctor to the location of the electrical stimulation path with regard to a head and a brain structure, which differ for each person.

The effects of the inventive concept are not limited by the above described effects, and other effects which are not described here may be clearly understood by those skilled in the art from the above disclosure.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A transcranial magnetic stimulation (TMS) stimulation navigation method, comprising:
   acquiring a stimulation target point to apply electrical stimulation on a brain of an object;
   acquiring information about a spatial distribution of a magnetic vector potential of a coil for TMS procedure;
   acquiring an optimal point, which has the highest magnetic vector potential in the spatial distribution, and an optimal vector, which is a normal vector where multiplication with a gradient at the optimal point becomes minimum among normal vectors where the optimal point is a start point;
   acquiring, based on the optimal point and the optimal vector, from the spatial distribution, an optimal stimulation condition for the stimulation target point, wherein the optimal stimulation condition is a condition where an intensity of a magnetic field applied to the stimulation target point by the coil for TMS procedure becomes maximum; and
   calculating, using the optimal point and the optimal vector, a position and direction of the coil, which satisfy the optimal stimulation condition for the stimulation target point, wherein according to the calculated position and direction of the coil, the coil is being placed on a particular position on a scalp of the object, and the particular position is the closest position among other positions on the scalp, from the stimulation target point, in the direction of the optimal vector from the optimal point,
   wherein the optimal point that is a position (x, y, z) having the highest value in a magnetic vector potential map, is calculated by Equation 1 below:

$$\max_{x,y,z} f(x, y, z), \quad \text{[Equation 1]}$$

where f denotes the magnetic vector potential map, and
wherein the optimal vector that is a vector v, is calculated by Equation 2 below:

$$\min_{x,y,z} \nabla f(\bar{x}, \bar{y}, \bar{z})^T v(x, y, z), \quad \text{[Equation 2]}$$

where $\nabla f(\bar{x}, \bar{y}, \bar{z})$ denotes a value acquired by differentiating f used when defining the optimal point at the optimal point $\bar{x}, \bar{y}, \bar{z}$, and v(x, y, z) denotes the normal vector in a direction of (x, y, z).

2. A transcranial magnetic stimulation (TMS) stimulation navigation method, comprising:
   acquiring a stimulation target point to apply electrical stimulation on a brain of an object;
   acquiring information about a spatial distribution of a magnetic vector potential of a coil for TMS procedure;
   acquiring an optimal point, which has the highest magnetic vector potential in the spatial distribution, and an optimal vector, which is a normal vector where multiplication with a gradient at the optimal point becomes minimum among normal vectors where the optimal point is a start point;
   acquiring, based on the optimal point and the optimal vector, from the spatial distribution, an optimal stimulation condition for the stimulation target point, wherein the optimal stimulation condition is a condition where an intensity of a magnetic field applied to the stimulation target point by the coil for TMS procedure becomes maximum; and calculating, using the optimal point and the optimal vector, a position and direction of the coil, which satisfy the optimal stimulation condition for the stimulation target point, wherein according to the calculated position and direction of the coil, the coil is being placed on a particular position on a scalp of the object, and the particular position is the closest position among other positions on the scalp, from the stimulation target point, in the direction of the optimal vector from the optimal point, generating and applying a matrix, shown in Equation 3 below, that is arranging a vector K and the optimal vector of the coil, $$R_x(\theta) = \begin{bmatrix} 1 & 0 & 0 \\ 0 & \cos\theta & -\sin\theta \\ 0 & \sin\theta & \cos\theta \end{bmatrix}$$

$$R_y(\theta) = \begin{bmatrix} \cos\theta & 0 & \sin\theta \\ 0 & 1 & 0 \\ -\sin\theta & 0 & \cos\theta \end{bmatrix}$$

$$R_z(\theta) = \begin{bmatrix} \cos\theta & -\sin\theta & 0 \\ \sin\theta & \cos\theta & 0 \\ 0 & 0 & 1 \end{bmatrix};$$

[Equation 3]

and calculating a location of the coil by using Equation 4:

Locdipole=$S+K*(D+P)$, [Equation 4]

where Locdipole denotes the location of the coil, S denotes the stimulation target point, K denotes the vector K, D denotes a distance between the stimulation target point and the closest position on the scalp from the stimulation target point, and P denotes a half of a thickness of the coil.

3. The TMS stimulation navigation method of claim 1, wherein the acquiring of the information about the spatial distribution includes:

acquiring information by visualizing the magnetic vector potential using a magnetic dipole according to a shape of the coil for TMS procedure.

4. The TMS stimulation navigation method of claim 1, further comprising:

simulating a state where electrical stimulation induced from the magnetic field of the coil for TMS procedure is propagated in the brain of the object, when the coil for TMS procedure is located at the calculated position in the calculated direction.

5. The TMS stimulation navigation method of claim 4, wherein the simulating includes:

acquiring a brain magnetic resonance imaging (MRI) image of the object;

generating a three-dimensional brain map of the object, the three-dimensional brain map being capable of simulating a process of delivering electrical stimulation to the brain of the object, based on properties of each of a plurality of regions included in the brain MRI image; and simulating a state where the electrical stimulation is propagated in the brain of the object, using the generated three-dimensional brain map.

6. The TMS stimulation navigation method of claim 5, wherein the generating of the three-dimensional brain map includes:

generating a three-dimensional stereoscopic image composed of a plurality of meshes, the three-dimensional stereoscopic image being capable of simulating a process of delivering electrical stimulation to the brain of the object.

7. The TMS stimulation navigation method of claim 6, wherein the simulating includes:

visualizing a state where electrical stimulation induced from the magnetic field of the coil for TMS procedure is propagated in the brain of the object, using the three-dimensional stereoscopic image.

8. A non-transitory computer-readable recording medium storing a computer program configured to be coupled with a computer hardware, and the program includes instructions to perform the method of claim 1.

9. The TMS stimulation navigation method of claim 2, wherein the acquiring of the information about the spatial distribution includes:

acquiring information by visualizing the magnetic vector potential using a magnetic dipole according to a shape of the coil for TMS procedure.

10. The TMS stimulation navigation method of claim 2, further comprising:

simulating a state where electrical stimulation induced from the magnetic field of the coil for TMS procedure is propagated in the brain of the object, when the coil for TMS procedure is located at the calculated position in the calculated direction.

11. The TMS stimulation navigation method of claim 10, wherein the simulating includes:

acquiring a brain magnetic resonance imaging (MRI) image of the object;

generating a three-dimensional brain map of the object, the three-dimensional brain map being capable of simulating a process of delivering electrical stimulation to the brain of the object, based on properties of each of a plurality of regions included in the brain MRI image; and simulating a state where the electrical stimulation is propagated in the brain of the object, using the generated three-dimensional brain map.

12. The TMS stimulation navigation method of claim 11, wherein the generating of the three-dimensional brain map includes:

generating a three-dimensional stereoscopic image composed of a plurality of meshes, the three-dimensional stereoscopic image being capable of simulating a process of delivering electrical stimulation to the brain of the object.

13. The TMS stimulation navigation method of claim 12, wherein the simulating includes:

visualizing a state where electrical stimulation induced from the magnetic field of the coil for TMS procedure is propagated in the brain of the object, using the three-dimensional stereoscopic image.

14. A non-transitory computer-readable recording medium storing a computer program configured to be coupled with a computer hardware, and the program includes instructions to perform the method of claim 2.

* * * * *